US011646107B2

(12) United States Patent
Forzoni et al.

(10) Patent No.: US 11,646,107 B2
(45) Date of Patent: May 9, 2023

(54) METHOD FOR GENERATING MEDICAL REPORTS AND AN IMAGING SYSTEM CARRYING OUT SAID METHOD

(71) Applicant: ESAOTE SpA, Genoa (IT)

(72) Inventors: Leonardo Forzoni, Florence (IT); Lorenzo Bessi, Florence (IT)

(73) Assignee: Esaote S.p.A., Genoa (IT)

( * ) Notice: Subject to any disclaimer, the term of this patent is extended or adjusted under 35 U.S.C. 154(b) by 292 days.

(21) Appl. No.: 16/894,178

(22) Filed: Jun. 5, 2020

(65) Prior Publication Data
US 2020/0395111 A1  Dec. 17, 2020

(30) Foreign Application Priority Data
Jun. 11, 2019 (EP) ..................... 19179503

(51) Int. Cl.
*G16H 15/00* (2018.01)
*G16H 30/20* (2018.01)
*G16H 40/63* (2018.01)
*G10L 15/07* (2013.01)
*G10L 15/18* (2013.01)
*G10L 15/25* (2013.01)

(52) U.S. Cl.
CPC ............ *G16H 15/00* (2018.01); *G10L 15/07* (2013.01); *G10L 15/1815* (2013.01); *G10L 15/25* (2013.01); *G16H 30/20* (2018.01); *G16H 40/63* (2018.01)

(58) Field of Classification Search
CPC ........ G16H 15/00; G16H 30/20; G16H 40/63; G16H 30/40; G10L 15/07; G10L 15/1815; G10L 15/25; G10L 15/26
See application file for complete search history.

(56) References Cited

U.S. PATENT DOCUMENTS

| 2002/0158967 | A1* | 10/2002 | Janick | G02F 1/1323 361/679.22 |
| 2009/0048866 | A1* | 2/2009 | Mahesh | G16H 15/00 705/2 |
| 2010/0171682 | A1* | 7/2010 | Chen | G16H 30/40 345/55 |
| 2014/0219500 | A1* | 8/2014 | Moehrle | G06T 7/0014 382/103 |
| 2014/0289675 | A1* | 9/2014 | Stading | G06F 16/3331 715/810 |
| 2015/0212676 | A1* | 7/2015 | Khare | A61B 6/467 715/771 |

OTHER PUBLICATIONS

European Search Report dated Dec. 16, 2019, which issued in corresponding EP Patent Application No. EP19179503.8.

\* cited by examiner

*Primary Examiner* — Paras D Shah
*Assistant Examiner* — Paul J. Mueller
(74) *Attorney, Agent, or Firm* — Dickinson Wright PLLC

(57) ABSTRACT

A method and a system for generating medical reports based on medical images are provided. The method and system are characterized by
carrying out an imaging examination on a target object;
visualizing the image or the sequence of images acquired during the execution of the imaging examination;
carrying out a report text generation step in parallel with the visualized image or sequence of images by using a speech recognition process; and
saving the report text by associating univocally the report text to the visualized image or to the sequence of images.

14 Claims, 13 Drawing Sheets

METHOD FOR GENERATING MEDICAL REPORTS AND AN IMAGING SYSTEM CARRYING OUT SAID METHOD

BACKGROUND

Today physicians perform examinations and then, after the patient is not anymore in the examination room, they prepare the report. This step is usually carried out between examinations of a patient and the following one or at the end of the day or even later on the following days. Similar workflow, even if related to notes supporting the acquired examination images and clips as well as annotations, measurements and bodymarks, is implemented usually also by sonographers, where an integration file is given to the physician to be able to do the report together with the images and clips review. Nowadays workflow is in series having first the full acquisition of the examination results and then, even after a quite long time, the report fulfillment in order to give it to the patient usually together with some images which are printed on paper or similar support or which are provided in electronic format.

Drafting the reports is the most time-consuming activity performed after carrying out the examination.

Speech recognition is commonly used in picture archiving and communication system(s) (PACS) where radiologists and physicians perform diagnosis on imaging-based acquisitions. Reporting rooms are usually equipped with several screens and a speech recognition system where the speech of the physician is transformed in the report text automatically as the physician goes through the acquired images (which can be CT, MRI, X-Ray, Ultrasound, etc.). Usually the physician speaks though a microphone, which can be also a multidirectional one (that is, no need to keep it close to the mouth).

Speech recognition has been already implemented on board on Ultrasound Systems for their use by voice activation. Such technology usually needed a headset microphone to work properly. The use of speech recognition for Ultrasound Systems was implemented in order to reduce the need to operate manually the system control panel, anyway its use was limited especially due to the fact it was generally considered not satisfactory to "talk to the Ultrasound system" with short words, usually pronounced straightforwardly such as "Freeze!", "Save!", "Color!", etc.) with the patient present.

SUMMARY

An object of the present disclosure is to provide a method and an imaging system carrying out said method which can help in increasing the everyday productivity optimizing the workflow for carrying out the examination and the associated preparation of the report.

A further object is to provide for a method and a system able to avoid anxiety and strange patient reactions, leaving the physician free to elaborate the report.

Still a further object is to provide for a method and an imaging system allowing to carry out the preparation of the report in an automatic way leaving the physician the less work as possible for determining the text of the report.

According to a first aspect a method is provided for generating medical reports based on medical images, which method comprises:

carrying out an imaging examination on a target object;
visualizing the image or the sequence of images acquired during the execution of the imaging examination;
carrying out a report text generation step in parallel with the said visualized image or sequence of images by using a speech recognition process;
saving the said report text by associating univocally the said report text to the visualized image or to the said sequence of images.

The speech recognition is used to create the report, or the integrative note related to the acquired images and clips—in case of a sonographer operating the system directly while performing the acquisition. Thus, the above method approaches the diagnosis in a "see and fulfill" modality therefore saving time due to the performing of the image acquisition and the reporting in an almost parallel way. The above method satisfies the necessity set by the productivity requirements of modern healthcare where long lists of patients, economical constraints and increased population age, are all forces which increase the attention to time saving and quick and confident diagnosis.

Many different embodiments of the speech recognition process and of the speech recognition system can be applied in combination with the present method. Current existing speech recognition systems comprises a speech recognition processor and a speech recognition input device such as one or more microphones.

Starting of the speech recognition process can be caused by a command given by the user or by an image recognition system acquiring and analyzing images of the face of the speaker and determining when the speaker begins to speak. Such image recognition processes can be also used for recognizing words or commands which are given by the user during silenced speaking (i.e., no sound is audible or produced while the user is speaking).

According to still another aspect which satisfies the privacy needs addressed above, an interactive, self-fulfilling reporting process is provided which completes the speech recognition process. To such extent the report text generation step may comprise an interactive reporting process which automatically populates statements into a corresponding text reporting region based on the speech recognition process.

According to an embodiment, the method provides in combination with the speech recognition steps an interactive text completion step consisting of suggestion to the speaker of a series of possible sensitive sentence completion parts.

Such sentence completion parts are univocally associated with a sentence completion tag, the said tag being an alphanumeric key and the operator can choose the sentence completion part to be added to the text generated by speech recognition at the correct position of the said text by selecting the corresponding tag by pronouncing the said alphanumeric key of the said tag.

An embodiment provides for a method for generating diagnostic reports based on diagnostic images comprising:

carrying out an imaging examination on a target object;
visualizing the image or the sequence of images acquired during the execution of the imaging examination;
carrying out a report text generation step in parallel with the said visualized image or sequence of images, for example by using a speech recognition process;
saving the said report text by associating univocally the said report text with the visualized image or to the said sequence of images, in which text completion tags are provided at selected parts of the text and each tag being associated with a list of possible parts of the text of the report relating to the description of the results of the analysis of the examination results, each element of the said list being identified by a unique identification key, the said key allowing to vocally select the part of the text associated with a specific key and the said list being either automatically visualized to the speaker at a certain part of the text of the report or being recalled by the speaker by a voice command, the said part of the text associated with the selected key being inserted in the text of the report at the corresponding position of the text.

When analyzed in relation to their structure and the content, the examination-based reports have to a large extent a sort of common text construction and common alternatives of the possible description of the diagnosis outcomes resulting from the examinations. This is mainly because the practice of copy and paste is widely used in drafting the reports in order to spare time, so that many parts of the text are at least similar in relation to structure and content in the different drafts of the report. Also when considering the possible outcomes of the analysis of the examination these outcomes are related to the anatomic district under examination and the alternatives are almost limited and well defined also from the point of view of the textual expression.

Therefore, according to a further embodiment, the method comprises the following step for determining the position, the number and the content of each tag and corresponding text completion:

selecting an anatomic district and/or an examination protocol and/or a specific pathology;
providing a plurality of different reports based on the examination of the above selected anatomic district and/or an examination protocol and/or a specific pathology;
providing an algorithm for carrying out a semantic analysis of a certain number of the said reports and determining different parts of the text which are almost similar from one report to the other and classifying the said part of the text as parts which can be recalled as collateral text parts to the parts of the text describing the different results of the diagnosis based on the examination results and which part of the text are completion parts of the said collateral part;
associating with the part of the text which is collateral to the said completion parts of the text describing the different results of the diagnosis based on the examination results tags at predetermined points each tag being related to a list of the said completion parts of the text describing the different results of the diagnosis based on the examination, associating with each of the said completion parts of the text describing the different results of the diagnosis based on the examination a unique key that can be used as a command for selecting and recalling and inserting the corresponding completion part of the text in the collateral part of the text at the position determined by the tag.

Different algorithms can be used and are known such as those related to Artificial Intelligence capable of learning from a database of known cases, such as nonlinear classifier, neural networks, genetic algorithm and other algorithms and also combination of one or more of the said algorithms.

According to a further embodiment, each report of the said plurality of different reports based on the examination of the above selected anatomic district and/or an examination protocol and/or a specific pathology is further associated with the physician or the sonographer who has generated the report and the algorithm can be taught to recognize automatically or by command the said specific physician or sonographer and suggest a collateral text or at least parts of the said collateral text and the corresponding tags and the list of examination results which are generated by analyzing essentially the reports of the said physician or sonographer.

Thus the reports are automatically tuned on the semantic and style of a specific user drafting a report.

Still according to a further embodiment, a link is generated between the content of the image and at least the completion part of the text describing the results on the corresponding image or sequence of images, the link being such that when in a report the said completion part or the related tag is selected the corresponding image or sequence of images is automatically retrieved and visualized or vice versa when a certain image is analyzed the list of possible completion part of the text is visualized.

According to a further improvement, the method provides the step of carrying out an image recognition step in which the content of the image is automatically identified and recognized, a link being provided between the said image and a completion text suggestion corresponding to the recognized content of the image.

According to still a further variant or another example embodiment, the link between the content of the image and at least the completion part of the text describing the results on the corresponding image or sequence of images, is such that when a certain image is selected the corresponding list of alternatives of the completion text depending on the results of the examination is visualized to the user and the user can carry out a selection of the said completion text.

Many alternatives of the above generic method steps can be provided.

An embodiment of the method according to one or more of the above variant example embodiments, provides for the following steps:

a) a first report database generation step comprising the steps of:
   a1) providing the text of a plurality of reports and of the corresponding examination results on which the report is based and which are in the form of images;
   a2) classifying the plurality of reports by carrying out a content and semantic analysis of the content of the reports and determining the parts of the text of the report which describe in text format the results based on the content of the images and the parts of the text which describes collateral features defining the target of the examination and/or the kind of examination and/or the examination protocol and/or the anatomic district;
   a3) generating a list of alternatives of the said parts of text of the report which describe in text format the results based on the content of the images, using the said part of text as completion parts which can be selected and inserted in the collateral part of the text;
   a4) inserting tags at predetermined points of the collateral part of the text for automatically signaling to the user drafting a report that at this point the text can be completed by means of a list of text completion parts generated according to the previous step;
   a5) defining user commands or automatic commands for visualizing the said list of text completion parts when the drafting of the collateral part of the text has reached a corresponding tag;
   a6) inserting in the draft of the report the completion part of the text selected by the user from the said list in the drafted text;
   a7) saving and/or outputting the drafted text.

According to a further feature, the method can provide for generating a link between the said completion parts of the text related to a list and the images showing the results described by the said completion part of the list, the said link being transitive such that when reading a report the corresponding image is shown when a completion part of the text is selected and vice versa when visualizing an image the corresponding completion part of the text chosen from the above list to be inserted in the corresponding report is shown together with the image.

A further improvement provides for the steps of generating a database in which the data related to the content of each image is associated with each image the said data comprising one or more of the following data: the kind of image and/or the anatomic district and/or the pathology and/or the examination protocol and/or the image acquisition protocol and automatically determining the completion part of the text based on the image content by analyzing an image automatically determining the content of the said image and automatically selecting from the database the at least one suggestion among different possible completion part of the text.

The above disclosed embodiments of the method are all related to the use of speech recognition technologies directly implemented on board the imaging device, for example such as a CT scanner, an Ultrasound scanner or an MRI scanner or similar devices.

With a multidirectional microphone which enables the operator to speak without the need to handle the microphone—impossible while performing for example an ultrasound examination. A headset microphone would be anyway necessary in case of elevated noise in the scanning area or of preferred by the operator.

The speech recognition is used to create the report or the integrative note related to the acquired images and clips—in case of a sonographer operating the system directly while performing the acquisition.

Due to the problem of privacy and in order to avoid anxiety and "strange" or unexpected patient reactions, an interactive, self-fulfilling reporting system completes the speech recognition tool for intelligent reporting.

The interactive report completion method consists in the suggestion to the operator of a series of possible "sensitive" sentence completion tags. Such tags can be chosen by the operator pronouncing a number or another vocal key associated with them or selecting them on a proper list available on any interactive user interface available on the imaging system such as typically a Touch Screen-based user interface.

The smart tag insertion can be also requested by the operator just pronouncing a "special word" or "special sentence" such as "Tag Request". In this case a proper organization of the tags as subgroups within the system such as in an interactive and intelligent database, can be highly beneficial in terms of quick resizing of the whole possible tag choices, within a more restricted and targeted sub-set, in line with the operator tag request insertion proposal.

The report as well as the suggested tags can be visible on the main monitor of the system, on one side with respect to the acquired image or images.

As disclosed by the above embodiments, such tags can also be inserted, together with their related full sentence, on the acquired image or clip. Moreover, the related image or clip can also be linked (tagged) to the corresponding sentence of the report (due to real-time acquisition and in parallel reporting, the two entities of acquired images and clips and report sections can be also linked two-way the one to the other:

going through the report, having the automatic pop up of the related acquired files;

scrolling the acquired images and clips, having the related sections of the report popping up).

The population/collection of the report with the proper tags can be achieved using 3 main methods:
1) auto fulfillment performed by the operator (before the examination, and performed once with the exception of addition and completion of the desired list of tags to be suggested during the report creation);
2) artificial intelligence based method which scans several databases of image reports and, after a learning phase where it is taught about the sensitive tags and when the context multiple selection has to be proposed, can perform the tags suggestion without any previous indication of the operator;
3) Artificial Intelligence-based technology with the addition of the auto-adaptation of the operator report after report is applied in order to optimize the number of suggested tags to speed up the tag selection and report completion.

The intelligent reporting technology supports multi-language capabilities in line with the multi-language possibilities of the general user interface of the imaging systems and scanner provided at the state of the art.

According to a further aspect, the present disclosure relates to a system for generating diagnostic reports and particularly to an imaging system carrying out the said method.

According to an embodiment, the system comprises:
a scanner unit for acquiring data from a target object;
a processing unit for generating image data from the data acquired by the scanner unit;
at least one monitor for visualizing one or more of the said images and/or a time sequence of the said images;
a user interface comprising input devices for selecting commands from a list of commands visualized on the said monitor and/or for inputting data or commands and output devices such as a monitor,
the system further comprising:
a word processor for generating text in digital format;
the said word processor comprising an input for inputting text and/or commands and output for showing the inputted text and/or the available commands;
a memory in which a database of a plurality preconfigured text of reports is saved and from which one or more of the said reports can be retrieved and put ready to be inserted in the report by user selection and insertion commands;
the said database being configured such that each one of the pluralities of report texts is divided in a collateral part of text which content is not directly related to the content of the image or images and in completion part of texts describing the content of each image according to different alternatives possible for the said content;
the said part of texts being associated with selection keys and the collateral part of texts being provided with tags at the point of insertion of a completion part of texts, the said tags automatically suggesting a completion part of the text by visualizing a list of different drafts of completion texts or the said tags signaling to the user that a list of completion texts is available and can be retrieved and visualized by a command;
a memory for saving the generated report formed by the combination of the chosen collateral and completion part of texts.

According to a further feature of example embodiments of the system, a database generation unit may be provided in combination with the above disclosed system which database generation unit comprises a classifier processor configured to analyze different existing reports and the corresponding images on which the report has been drafted and for identifying collateral parts of text and completion part of text, the said classifier being configured to generate links between the images and the corresponding collateral part of texts and completion part of texts.

According to a further feature of the example embodiments, the system has an input for the word processor with a speech recognition and/or text dictation unit comprising at least one microphone.

Still according to a further feature of the example embodiments, the imaging system is provided with two or more monitors one of which for replicating the image output of the system, as well as the related graphics and data, the part of the intelligent real-time reporting and the smart tags suggestion and selection being not reported on the secondary monitor while hidden or substituted by a different graphics/contents.

In a variant example embodiment, anti-visibility filters or special screen highly sensitive direction polarization both for the main screen and the touch screen/interactive user interface of the system, can be added to the system for an intelligent reporting methodology implemented maintaining the full privacy protection of the patient also in case of crowded scanning rooms when also the presence of relatives or caregivers of the examined patient, are allowed to be present while scanning (and, therefore, while fulfilling the intelligent report in parallel with the scanning activity).

While multiple embodiments are described, still other embodiments of the described subject matter will become apparent to those skilled in the art from the following detailed description and drawings, which show and describe illustrative embodiments of disclosed inventive subject matter. As will be realized, the inventive subject matter is capable of modifications in various aspects, all without departing from the spirit and scope of the described subject matter. Accordingly, the drawings and detailed description are to be regarded as illustrative in nature and not restrictive.

Figure 1:
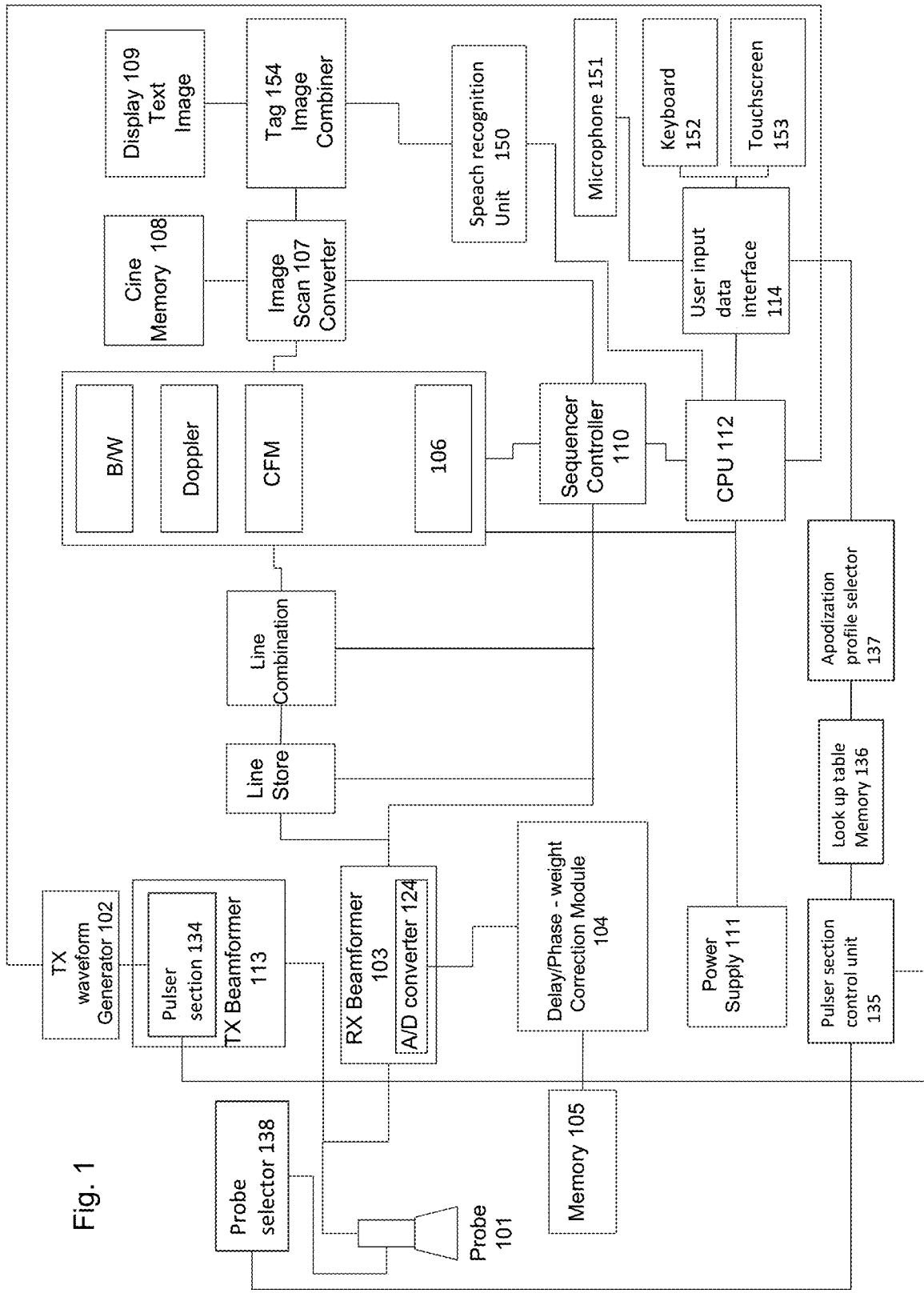
FIG. 1 is a block diagram of an embodiment herein in which the imaging system is an ultrasound system.

FIG. 1 illustrates a high-level block diagram of an ultrasound system implemented in accordance with embodiments herein. Portions of the system (as defined by various functional blocks) may be implemented with dedicated hardware, analog and/or digital circuitry, and/or one or more processors operating program instructions stored in memory. Additionally, or alternatively, all or portions of the system may be implemented utilizing digital components, digital signal processors (DSPs) and/or field programmable gate arrays (FPGAs) and the like. The blocks/modules illustrated in FIG. 1 can be implemented with dedicated hardware (DPSs, FPGAs, memories) and/or in software with one or more processors.

The ultrasound system of FIG. 1 includes one or more ultrasound probes 101. The probe 101 may include various transducer array configurations, such as a one-dimensional array, a two-dimensional array, a linear array, a convex array and the like. The transducers of the array may be managed to operate as a 1D array, 1.25D array, 1.5D array, 1.75D array, 2D array, 3D array, 4D array, etc.

The ultrasound probe 101 is coupled over a wired or wireless link to a receive beamformer (RX) indicated by 103 and to a transmission beamformer (TX) indicated by 113. The TX and RX beamformers may be implemented together or separately. The beamformer 113 supplies transmit signals to the probe 101 and the beamformer 103 performs beamforming of "echo" receive signals that are received by the probe 101.

A TX waveform generator 102 is coupled to the beamformer 103 and generates the transmit signals that are supplied from the beamformer 103 to the probe 101. The transmit signals may represent various types of ultrasound TX signals such as used in connection with B-mode imaging, Doppler imaging, color Doppler imaging, pulse-inversion transmit techniques, contrast-based imaging, M-mode imaging and the like. Additionally, or alternatively, the transmit signals may include single or multi-line transmit, shear wave transmit signals and the like.

The beamformer 113 performs beamforming of the transmit beams in order to focalize the transmit beams progressively along different adjacent lines of sight covering the entire ROI.

According to the present embodiment, the transmit waveform generator provides the settings of the electric excitation signals of the transducer elements of the array of the probe. The said settings are related to parameters as the frequency of the excitation signal, the number of duty cycles of the said signal, the delays to be applied to each excitation signal of each of the transducer elements selected to be excited to emission of an ultrasound signal, in order to cause the said acoustic signals to be focused on a region or on a point located in the target region. Focusing consists in this case to delay the acoustic signals emitted by each transducer element relatively to the other signals emitted by the other acoustic elements in such a way as to cause the said signals to combine constructively at the focus point or at a region to which the ultrasound beam is to be focused.

The signals generated by the waveform generator 102 are fed separately to the corresponding transducer element. The summing of the delays is applied in the TX beamformer 113. According to the present embodiment, the TX beamformer comprises or is provided in combination with a pulsar section 134. This section generates a pulsed electric excitation signal having a certain number of cycles corresponding to a sequence of pulses of certain number of pulses. The pulses have a square waveform and have a predetermined length and a predetermined amplitude.

The pulser section 134 comprises or operates in combination with a modulator modulates each or at least part of the pulsed electric signals by feeding to the transducer elements only a predetermined portion of the pulses of the said pulsed electric signals.

According to the present embodiment this is carried out by cutting the duration of each pulse of the pulsed electric excitation signal according to a predetermined time period.

According to an embodiment herein the cut off of the pulses of the excitation signals is carried out by shutting off or interrupting the feeding channel of the excitation signal to the corresponding transducer element.

The time period of cutting the duration of each pulse is chosen in such a way to control the overall energy applied to probe's elements so that the acoustic energy field generated by the transmitted ultrasound pulse by the probe is subjected to apodization showing a predetermined profile in which the side lobes are significatively reduced or suppressed.

Given a certain apodization profile, the pulse cut off periods can be calculated theoretically, selectively for each transducer element or the said cut off periods can be taken from an experimentally generated database in which a certain apodization profile is associated univocally with a certain set of cut off periods. In the present example of FIG. 1, both alternatives are possible.

A pulser control unit 135 is provided which is configured by a control program to operate the pulser section unit 134 as described above. The data relating to the cut off periods of the excitation signals related to each different transducer are taken either from a look up table saved in a memory 136 or this data is inputted by the user through the User input interface 114.

According to a further feature which is provided in the present example, an apodization profile selector 137 may be provided allowing either the user and/or the technicians of the producer to select a certain desired apodization profile of the acoustic wave transmitted by the probe. In this case the look up table may be constructed in such a way as comprising different apodization profiles each one associated with the set of cut off periods of the excitation signals fed to the corresponding transducer elements.

In the case that the apodization profile is factory preset, the pulser section control unit may be configured to automatically find and load the cut off periods related to the set apodization profile.

According to still a further embodiment, which is shown in the example of FIG. 1, but which could also not be provided, the probe 101 can send data to a probe selector 138 when the said probe is connected to the system. According to factory set optimal default settings, the system can automatically select the probe type, the corresponding look up table in the memory 136 and the optimum default apodization profile, thus allowing the pulser section control unit 135 to automatically receive or read the corresponding settings of the cut off periods.

In alternative embodiment, the probe is provided with a memory in which the probe type is saved and which memory can be read by the system at the connection of the probe. The probe selector 138 can thus read automatically the probe type and operate the automatic selection of the optimal default look up table, the default apodization profile and the corresponding default settings of the cut off period.

Further to the transmit beam generation section, the system comprises the receive beamformer 103 performing beamforming upon received echo signals to form beamformed echo signals in connection to pixel locations distributed across the region of interest. For example, in accordance with certain embodiments, the transducer elements generate raw analog receive signals that are supplied to the beamformer. The beamformer adjusts the delays to focus the receive signal along one or more select receive beams and at one or more select depths within the region of interest (ROI). The beamformer adjusts the weighting of the receive signals to obtain a desired apodization and profile. The beamformer applies weights and delays to the receive signals from individual corresponding transducers of the probe. The delayed, weighted receive signals are then summed to form a coherent receive signals.

The beamformer 103 includes (or is coupled to) an A/D converter 124 that digitizes the receive signals at a selected sampling rate. The digitization process may be performed before or after the summing operation that produces the coherent receive signals.

Optionally, a dedicated sequencer/timing controller 110 may be programmed to manage acquisition timing which can be generalized as a sequence of firings aimed at select reflection points/targets in the ROI. The sequence controller 110 manages operation of the TX and the RX beamformer 103, 113 in connection with transmitting ultrasound beams and measuring image pixels at individual LOS locations along the lines of sight. The sequence controller 110 also manages collection of receive signals.

One or more processors 106 perform various processing operations as described herein.

According to an embodiment herein the sequencer 110 controls the beamformer in order to generate and transmit a plurality of transmit beams which are focalized in such a way as to show an aperture or a beam width encompassing a certain number of line of sights ore of receive lines. The transmit beams of the said plurality being progressively laterally shifted along the array of transducer elements of the probe and thus along the ROI for scanning the entire ROI. A certain line of sight or a certain receive line will be encompassed by a certain number of different transmit beam of the said plurality as long as the said line of sight position or the said receive line position falls within the aperture of the said transmit beams or within the width of the said transmit beams. Thus for a reflecting point on a certain receive line or line of sight having a certain line position within the ROI and relatively to the transducer array of the probe a certain number of receive signals contributions are received each one deriving from a different transmit beam whose center transmit line having different lateral shifts relatively to the said reflecting point and to the corresponding receive line.

The receive data relatively to the echoes from the said reflecting point is a combination of the contributions of the receive signals from the said reflecting point deriving from the said certain number of transmit beams.

In accordance with embodiments herein, the beamformer 103 includes an input that is configured to be coupled to an ultrasound probe 101 and receive signals from transducers of the ultrasound probe 101. The memory 105 stores time delays to align contributions of reflection signals received by the transducers of the array of the probe 101 from the reflectors in the ROI. The memory 105 also stores phase corrections to correct phase differences of the receive signals contributions for each transducer element and deriving from each of the said certain number of differently laterally shifted transmit beams relatively to the receive line or line of sight on which the said reflector point is located.

A delay/phase correction (DPC) module 104 is coupled to the memory 105 and provides various delays and corrections to the beamformer 103. For example, the DPC module 104 directs the beamformer 103 to apply time delay and phase correction to the receive signals to form delayed receive signals. The beamformer 103 then sums, in a coherent manner, the delayed receive signals to obtain a coherent receive signal in connection with a reflection point or a reflection target.

Optionally, the memory 105 may store a common phase shift correction in connection with multiple channels. Different phase shift corrections may be stored in connection with various corresponding channels in the case of multiple receive signals are received along a common receive line position but due to a certain number of different transmit beams each one having a laterally shifted transmit center line and an aperture or width encompassing the receive line position. The memory 105 may also store weights such as apodization weights and/or RTB weights.

As explained herein, the beamformer 103 (circuitry) is configured to apply contemporaneously to each receive signal contribution of each transducer element from a reflection point a beamforming focalization delay and a phase shift equalization delay so called RTB delay. The said beamforming focalization delay being calculated basing on the time of arrival of the said signal contribution to a transducer element when traveling from the reflection point to the said transducer element and the said phase shift equalization delay being determined according to the difference in phase of the wave front reaching the reflecting point relatively to the phase of the wave fronts reaching the same reflecting point and being of further transmitted beams which are laterally shifted each other.

Optionally, the memory 105 may store a pre-calculated table, where the pre-calculated table comprises real times of arrival of the receive signals relative to a predetermined reflection point. Optionally, the processor 106 may be configured to calculate real times of arrival of the receive signals relative to a predetermined reflection point. Optionally the memory 105 may store a pre-calculated table, where the pre-calculated table comprises pre-calculated phase shift equalization delays to be applied contemporaneously to the beamforming focalization delays to the receive signals of a receive line along a certain line of sight or a certain receive line position deriving from a certain number of transmit beams being differently laterally shifted relatively to the said receive line position, the number of the said transmit beams being set by setting a certain aperture or lateral width of the said transmit beams. Optionally the memory 105 may store a pre-calculated table of the said phase shift equalization delays which are pre-calculated for one or more of different transmit beams apertures or widths.

Optionally, the processor 106 may be configured to calculate the said phase shift equalization delays for one or more of different transmit beams apertures or widths.

Optionally, the beamformer 103 circuitry may further comprise an adder unit for adding the beamforming delays and the phase shift equalization delays (RTB delays) for the receive signal contributions deriving from each reflecting point.

In accordance with certain embodiments, at least a portion of the beamforming process may be implemented by the processor 106 (e.g., in connection with software RTB beamforming). For example, the memory 105 may store beamforming related program instructions that are implemented by the processor 106 to contemporaneously apply beamforming delays and phase shift equalization delays to the receive signals.

The processor 106 and/or CPU 112 also performs conventional ultrasound operations. For example, the processor 106 executes a B/W module to generate B-mode images. The processor 106 and/or CPU 112 executes a Doppler module to generate Doppler images. The processor executes a Color flow module (CFM) to generate color flow images. The processor 106 and/or CPU 112 may implement additional ultrasound imaging and measurement operations. Optionally, the processor 106 and/or CPU 112 may filter the first and second displacements to eliminate movement-related artifacts.

An image scan converter 107 performs scan conversion on the image pixels to convert the format of the image pixels from the coordinate system of the ultrasound acquisition signal path (e.g., the beamformer, etc.) and the coordinate system of the display. For example, the scan converter 107 may convert the image pixels from polar coordinates to Cartesian coordinates for image frames.

A cine memory 108 stores a collection of image frames over time. The image frames may be stored formatted in polar coordinates, Cartesian coordinates or another coordinate system.

An image display 109 displays various ultrasound information, such as the image frames and information measured in accordance with embodiments herein. The display 109 displays the ultrasound image with the region of interest shown.

A control CPU module 112 is configured to perform various tasks such as implementing the user/interface and overall system configuration/control. In case of fully software implementation of the ultrasound signal path, the processing node usually hosts also the functions of the control CPU.

A power supply circuit 111 is provided to supply power to the various circuitry, modules, processors, memory components, and the like. The power supply 111 may be an A.C. power source and/or a battery power source (e.g., in connection with portable operation).

Connected to the user input data interface there may be a keyboard 152 and/or a touchscreen 153 on which a virtual keyboard may be displayed and operating according a traditional keyboard.

Further data input devices can comprise one or more microphones 151 according the different alternatives described in the following description.

Vocal information inputted by the microphones can be interpreted by a speech recognition unit 150. This speech recognition unit 150 elaborates the vocal information recognizing the content and transforming it in digital information, like a text or in commands. The digital text provided by the speech recognition unit 150 may be sent to a combiner unit 154 which combines image related vocal data transformed in a digital text with the corresponding image generating a unique tag associated with the said text.

The combined tag, image and textual may be stored and/or printed on a screen 109.

According to an embodiment, the microphone 151 may be a multidirectional microphone which enables the operator to speak without the need to handle the microphone since handling a microphone would be nearly impossible while performing for example an ultrasound examination.

According to a further variant embodiment which can also be provided in combination with the above one, a headset microphone can be provided. Such kind of microphone would be advantageous in case of elevated noise in the scanning area.

According to an embodiment, the speech recognition is used to create a report or integrative notes related to the acquired images and clips directly while performing the acquisition.

According to embodiments herein, due to the problem of privacy and in order to avoid anxiety and "strange" or unexpected patient reactions, an interactive, self-fulfilling reporting system completes the speech recognition tool for intelligent reporting.

The interactive report completion method consists in the suggestion to the operator, of a series of possible "sensitive" sentence completion tags. Such tags can be chosen by the operator pronouncing a number associated with them or selecting them on a proper list available on any interactive user interface available on the Ultrasound system, such as typically a Touch Screen-based user interface 153.

The smart tag insertion can be also requested by the operator just pronouncing a "special word" or "special sentence" such as "Tag Request". In this case a proper organization of the tags as subgroups within the system (interactive and intelligent) database, can be highly beneficial in terms of quick resizing of the whole possible tag choices, within a more restricted and targeted sub-set, in line with the operator tag request insertion proposal.

The report as well as the suggested tags can be visible on the main monitor of the system, on one side with respect to the echographic image.

Such tags can also be inserted, together with their related full sentence, on the acquired image or clip. Moreover, the related image or clip can also be linked (tagged) to the corresponding sentence of the report (due to real-time acquisition and in parallel reporting, the two entities of acquired images and clips and report sections, can be also linked two-way the one to the other: going through the report, having the automatic pop up of the related acquired files; scrolling the acquired images and clips, having the related sections of the report popping up).

The population/collection of the report with the proper tags can be achieved using 3 main methods:
1) auto fulfillment performed by the operator, before the examination, and performed once with the exception of addition and completion of the desired list of tags to be suggested during the report creation.
2) artificial intelligence-based method which scans several databases of Ultrasound reports and, after a learning phase where it is taught about the sensitive tags and when the context multiple selection has to be proposed, can perform the tags suggestion without any previous indication of the operator
3) Artificial Intelligence-based technology of point 2 with the addition of the auto-adaptation of the operator report after report, in order to optimize the number of suggested tags to speed up the tag selection and report completion.

The intelligent reporting technology supports multi-language capabilities (e.g., in line with the multi-language possibilities of the general User Interface of the Ultrasound scanner).

Figure 13:
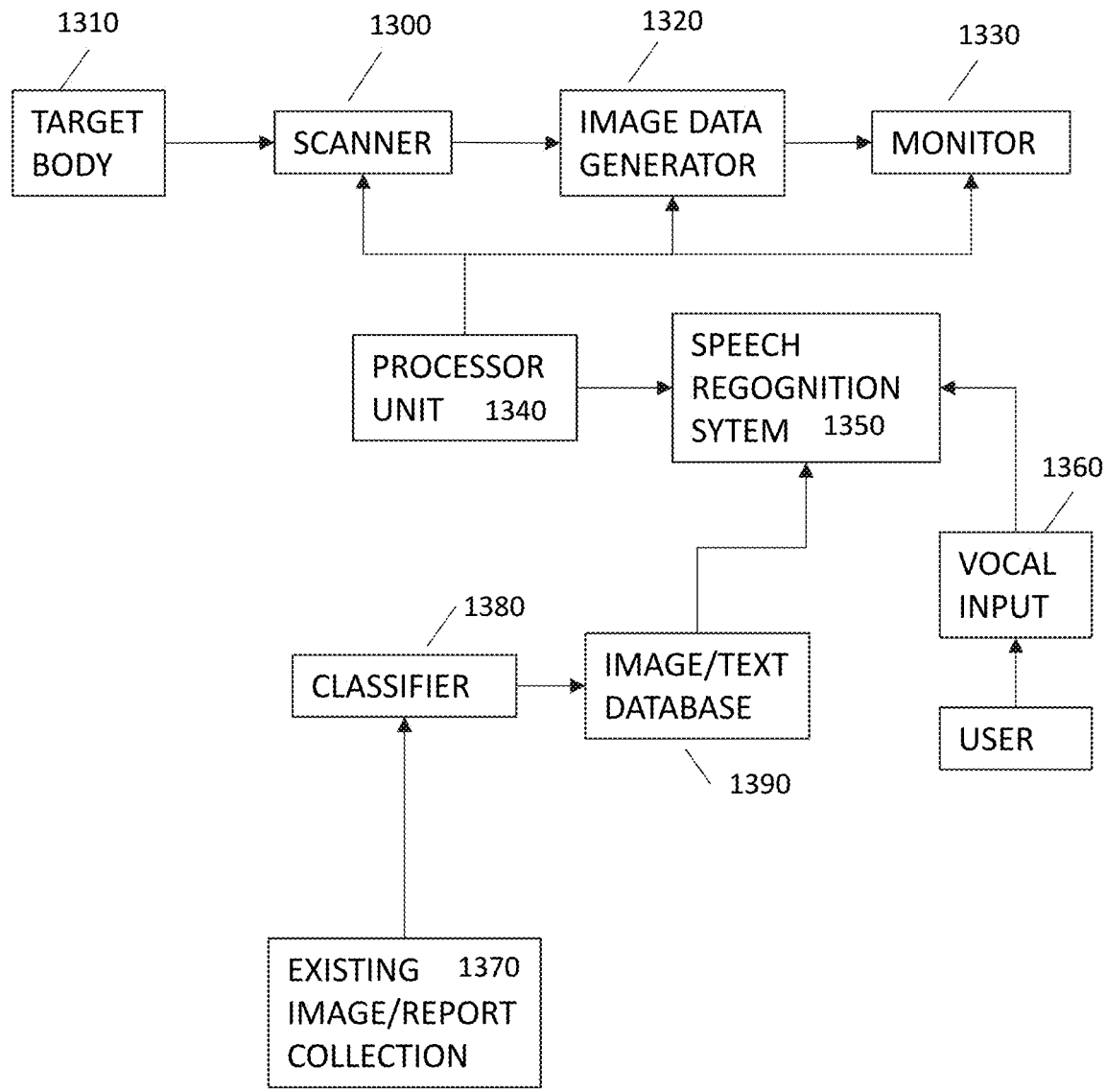
FIG. 13 show a block diagram of a generic imaging system operating according to embodiments herein.

As already mentioned in the description above, the method according to example embodiments herein may be applied in combination of different kinds of imaging systems and not being limited only to the specific example described in detail herein. FIG. 13 shows a high-level block diagram of a generic imaging system which is configured to be able to carry out the method according to embodiments herein.

Image data is acquired by a scanner 1300 operating on a target body 1310. The acquired signals are transformed in image data by an image data generator 1320 and saved and/or visualized on a monitor 1330. The processing chain from the signal acquired by the scanner 1310 to the monitor for visualizing images extracted by processing the acquired signals is controlled by a processing unit 1340. The processing unit 1340 controls also a speech recognition system 1350 which receives vocal inputs from a user through a vocal input device 1360. From an existing image/report collection 1370, by means of a classifier 1380, an image/text database 1390 can be constructed which database can be used to generate the suggestions to the user related to the parts of the report describing the specific meaning of the image which are pertinent to the said image.

Figure 2:
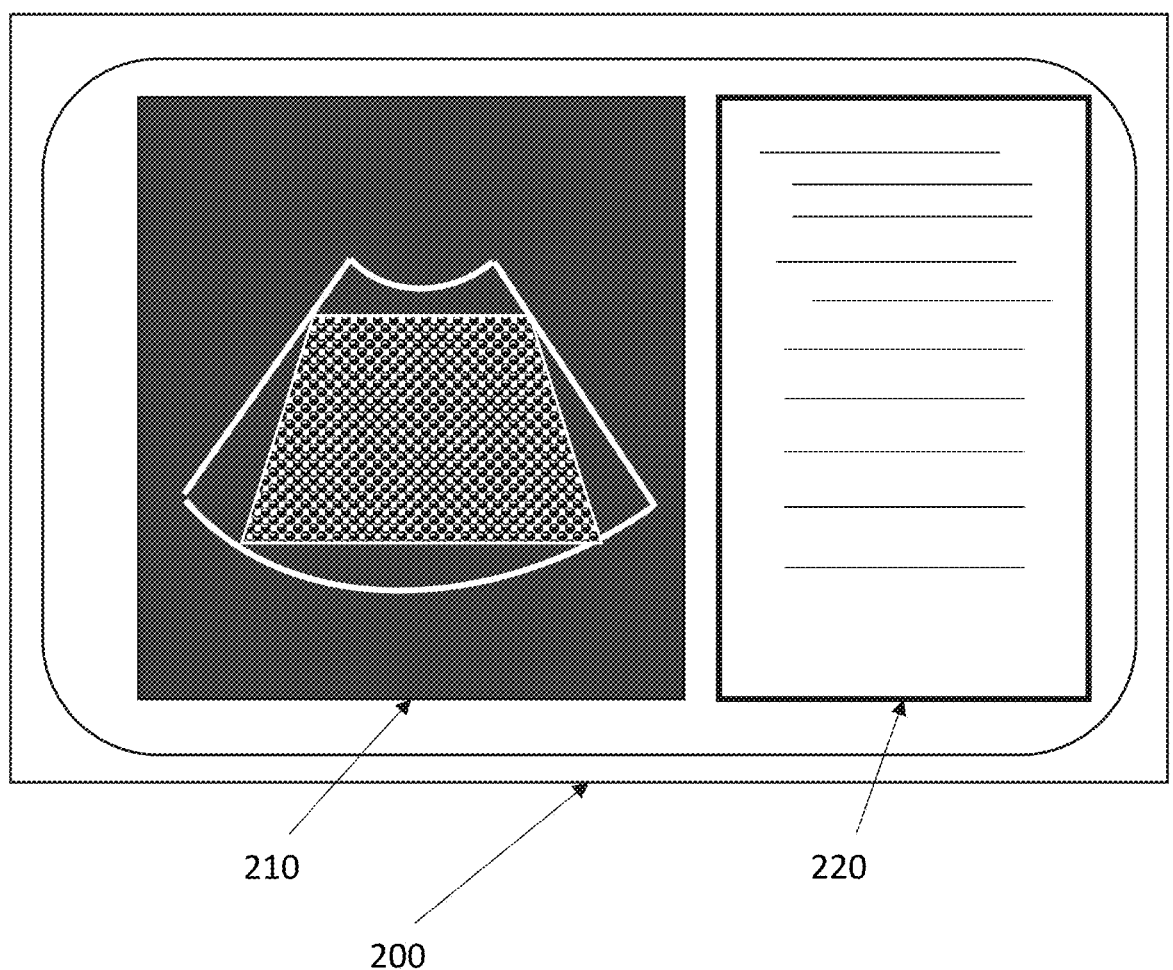
FIG. 2 is an example of the image and the report text visualized on the monitor screen of a system according to embodiments herein.

FIG. 2 shows an example of a report drafted as a digital text and displayed on the screen of a monitor beside the corresponding image acquired by the scanner, in this case by the probe of a system according to FIG. 1.

With 200 there is indicated the screen of a monitor which in this case is the monitor of an ultrasound system according to the imaging system described in detail without any prejudice of claiming the combination of whichever kind of imaging device.

On the area 210 of the screen the acquired image is displayed as in a traditional ultrasound scanner. Besides the said area 210, there is a further area on which a report may be printed which is based on the content of the image displayed on the left hand of the screen. The report area of the screen is placed besides the area for visualizing the acquired image or images.

Figure 3:
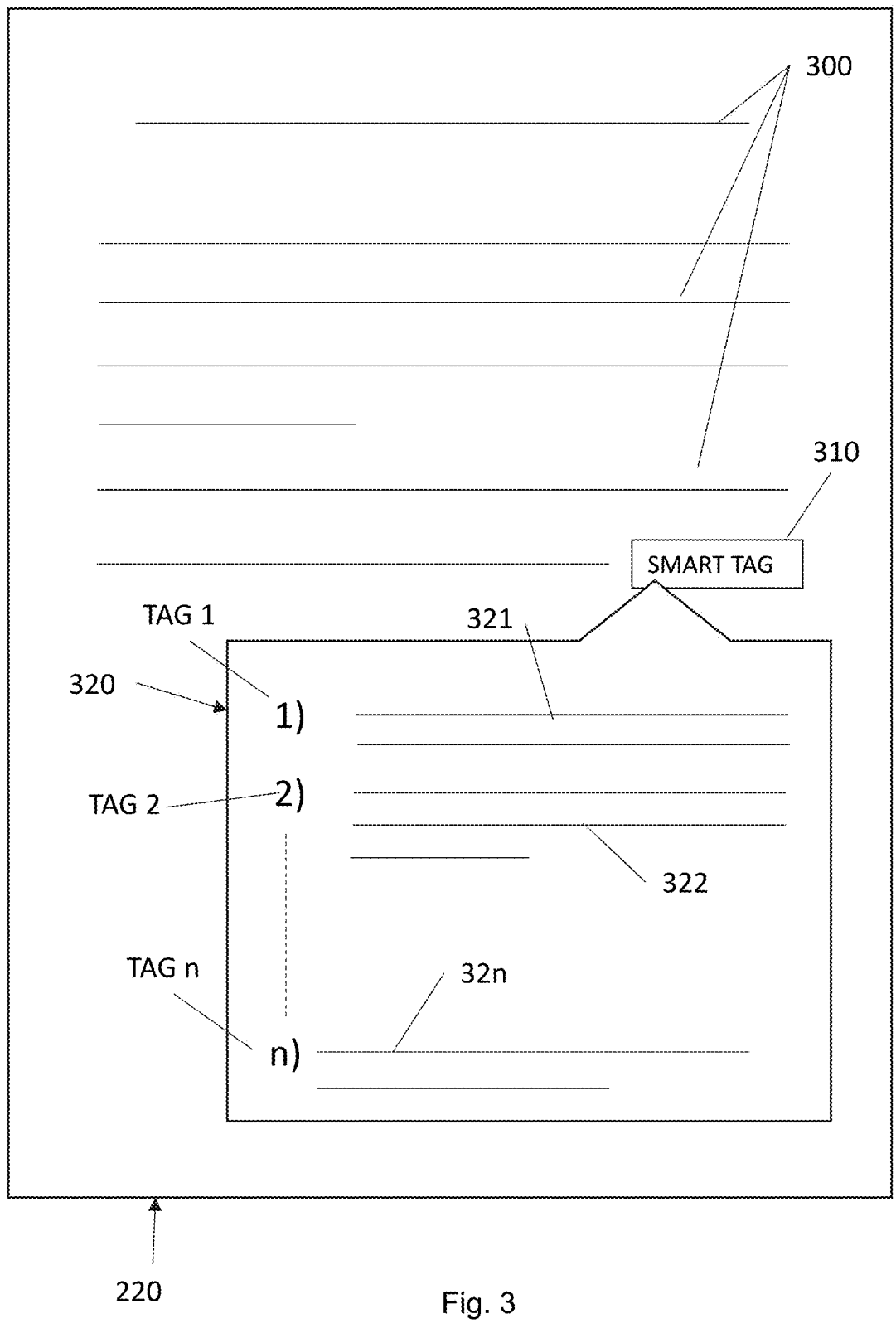
FIG. 3 is an example of the smart-tag text completion method according to embodiments herein.

The example of FIG. 3 describes with more detail the method according to an embodiment. Each report text is divided into a part of text which is collateral to the real diagnostic information. This specific diagnostic information is contained in a further part of the text which completes the collateral part of the text and which is specific to the kind of examination and to the condition or pathology investigated.

The collateral part of the text may be for example a description of the examination step end/or the general condition of the patient and/or the settings of the scanner and other general information.

The specific diagnostic text is relative to the description of the image relatively to the anatomic district examined and to the diagnostic interpretation of the image.

Since for nearly every kind of examination the outcomes of the diagnostic interpretation of the images and the description of these outcomes are essentially identical there is the possibility to offer to the user dictating the report a list of alternatives of the descriptive text and which are preconfigured.

At the points of the collateral part of text 300 where a diagnostic information has to be inserted, a smart tag 310 can be placed. When dictating a diagnostic text as a relation of the diagnostic activity the text is automatically transformed in a digital alphanumeric text by means of a speech recognition unit.

At the point where it is appropriate to insert the diagnostic relevant information extracted by interpreting of the images by the user and which information is in the form of a text completion part, the system may provide three different options according to three alternatives from which one option might be chosen by the user in the same system.

According to one alternative the user interface is provided with graphic commands for accessing a list of tags each one associated with a list of context specific text completion parts and of selection and insertion commands of a specific text completion part which describes in words the interpretation of the image made by the user. The said text completion and insertion commands allow the user to choose the appropriate text completion part from the list associated with a tag and to insert this at the appropriate point of the collateral part of the text already drafted by the speech recognition unit.

In case a list of text completion parts does not contain an appropriate description in words of the image interpretation a non-vocal input interface may be provided for the user, such as a keyboard, in order to allow the user to draft an appropriate text completion part.

This may be then inserted in the drafted report text at the pertinent point of the collateral part of the text dictated by the user using the speech recognition system and additionally this new text completion part may be saved and added to the list of text completion parts associated with the tag.

According to a further alternative which can be provided in combination with the previous one by means of a selection command, the tag selection and the text completion part selection and insertion commands may be of vocal kind using the speech recognition unit.

In accordance with a further variant which may be provided in combination and which can be alternatively activated by selection through the user interface of the system, the choice of the tags to be made available to the user is restricted to pertinent content of the text completion parts associated with the tag by previously inputting information data on the kind of examination and/or of anatomic district and/or organ to be examined.

This information data may be inputted by suggesting to the user by means of the user interface a list of examinations and/or of anatomic districts and/or of organs and by carrying out a selection by means of selection commands made available through the user interface.

Another variant embodiment which can be selectable and activated by the user can provide for automatically carrying out a semantic analysis of the collateral text part and automatically suggesting as a pop up either only the list of tags associated with a list of pertinent completion text parts or directly opening at the appropriate point of the collateral text the list of possible completion parts of the collateral text.

This last variant can be carried out by providing a semantic analyzer such as a semantic algorithm coded as a software and carried out by a processor unit in combination with a classification or predictive algorithm, which analyzes the collateral text part and determines the most appropriate tag comprising the list of pertinent alternative completion text parts.

FIG. 3 shows an example of the above embodiments being easily understood as an alternative to the one of FIG. 2.

The collateral text indicated at 300 might be simply dictated by the user and is transformed in written digital text by the speech recognition unit. "310" in FIG. 3 represents the smart tag which when addressed opens a list of tags indicated by Tag-1 to Tag-n. Each tag-1 to Tag-n opens when selected a list comprising at least one text completion part indicated by 321, 322, 32n which text completion parts are pertinent to the content of the collateral text 300 at the insertion point of the text completion part.

Figure 4:
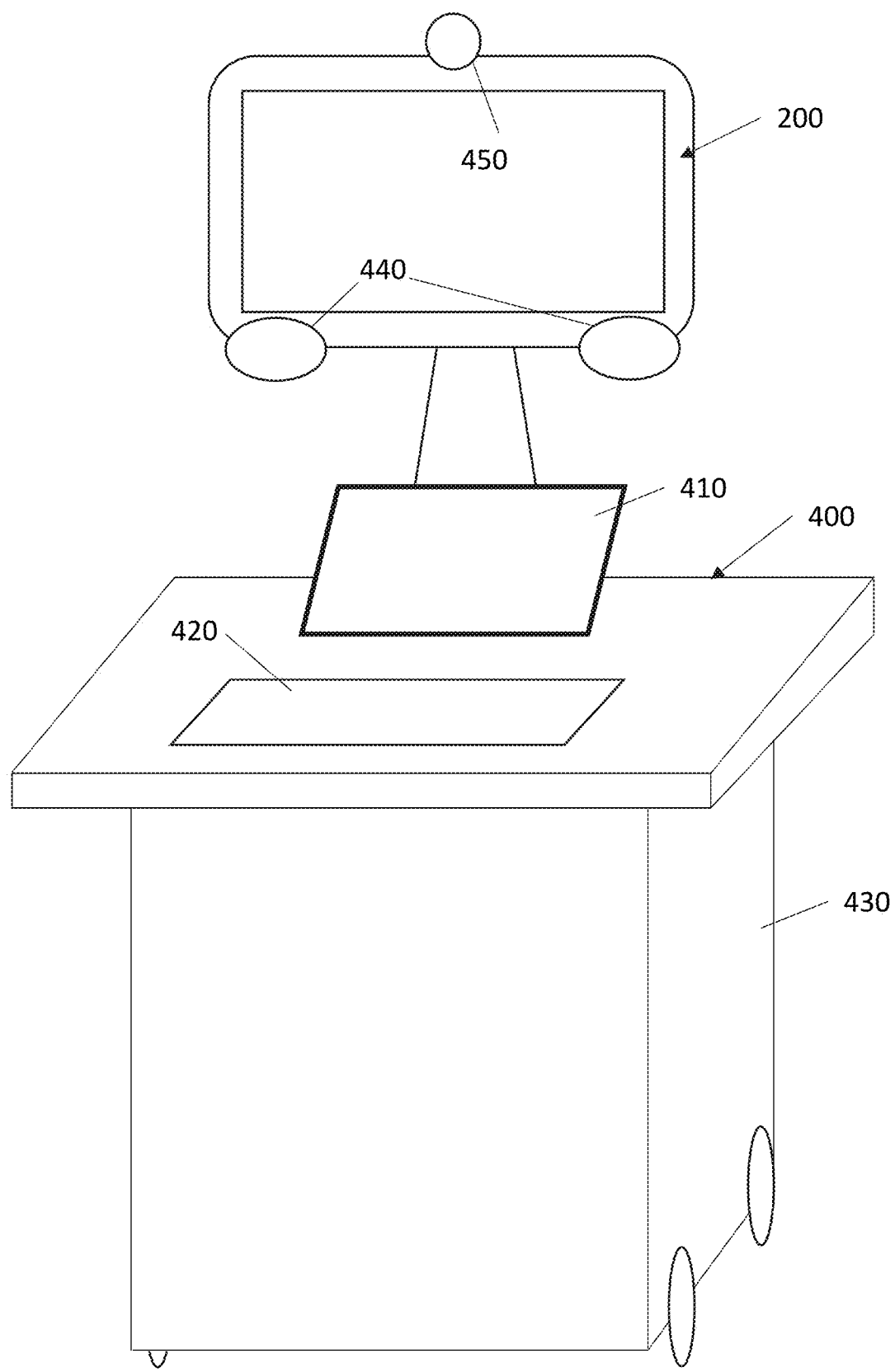
FIG. 4 is an example of an ultrasound system comprising the monitor outputs and the speech recognition inputs according to embodiments herein.

FIG. 4 illustrates an ultrasound system 400 comprising a carriage 430 containing the electronic units for controlling the ultrasound system and carrying out the ultrasound imaging. Furthermore, the carriage 430 may contain the speech recognition unit and the processor for executing a software comprising the instructions for configuring the said processor to carry out the method according to embodiments herein and to the one or more of the variant embodiments disclosed herein.

A non-limiting example of the said electronic units disclosed in FIGS. 6 to 9 and in the corresponding description.

Typically, as shown in FIG. 4, the system comprises a command and data input desk comprising for example various buttons or other controls and a keyboard. The said commands and input organs being indicated generically by 420.

The Ultrasound system comprises at least one monitor 200 or any other visualization device. According to an embodiment shown in FIG. 4 the system comprises two monitors 200 and 410, one of which can be of the so called touch-screen kind and may be used for showing the list of tags and the list of completion parts as well as for highlighting and selecting the tags and the associated list of text completion parts and for commanding the insertion the report draft of the selected text completion part.

Numerals 440 and 450 indicates one or more microphones for collecting the vocal inputs for the speech recognition system and/o for collecting visual inputs which are converted in commands by an image processing unit carrying out image recognition.

As an alternative to the more traditional user interfaces, the one operating by means of the image recognition processing unit allows the user to impart selection and insertion commands to the system in a vocal-less way by simply interpreting the labial movements of the user in pronouncing a command.

As an alternative, such image recognition-processing unit may also be provided for inputting additional text completion parts not provided into the list associated with one tag, allowing the user to draft the said text completion part by vocal-less dictation.

According to a further variant embodiment, the monitor 200 or 410 of further monitors connected to the ultrasound system 400 may be provided in combination with filters which renders illegible the part of the monitor or the monitor on which the report 220 is shown selectively to certain kind of persons looking at the monitor. This can be done by polarizing filters which in combination with spectacles allow to view the report only to persons provided with the said spectacle of by polarizing the screen of the monitor such that the screen or the part of it on which the report is printed cannot be seen under certain direction of view.

A further alternative which can be provided when a monitor is present which is set free for the view by the user is to prevent the printing of the report on this screen or to obscure the part of the said screen on which the report is printed.

According to a further feature, the method and the system provided for the possibility to link the images or certain views of the images acquired by the imaging system to the tags or the corresponding text completion parts.

Figure 5:
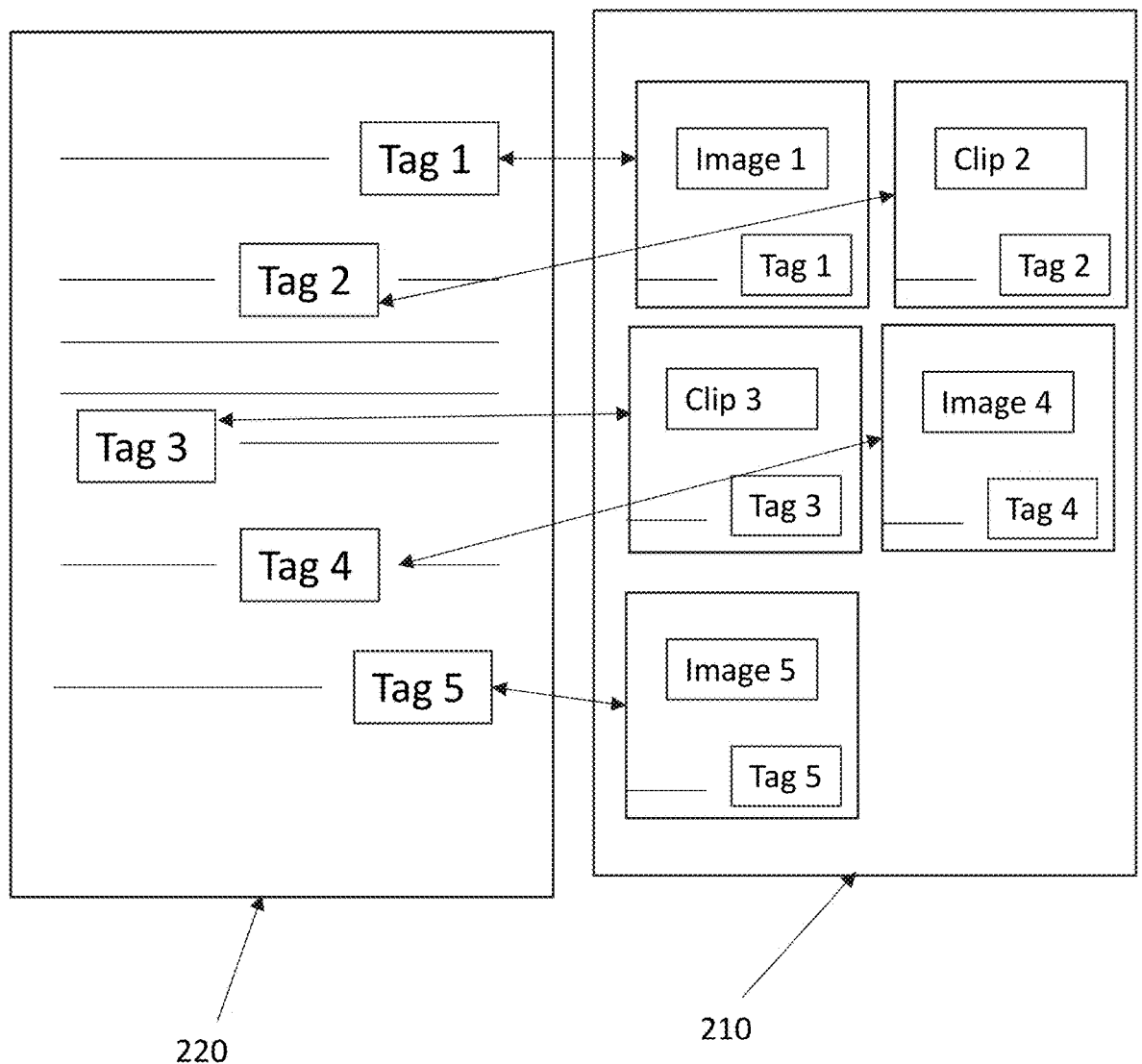
FIG. 5 is a diagram showing the links between the tagged completion text parts of the report and the corresponding images of the examination on which the report is based.

One possible embodiment is shown in FIG. 5 on the left side the report text 220 is shown provided with a collateral text parts and with completion text parts associated with different tags as Tag1, Tag2, Tag3, Tag4 and Tag5 at the pertinent points of the collateral text. The screen or the screen part 210 is the one on which the images are printed. Each image is associated with a tag. For simplicity herein the case is illustrated in which each image corresponds to the verbal content of the completion part of the tags of respectively one tag of the tags 1 to 5. Nevertheless, an image may be associated with more than one tag and vice-versa (e.g., a tag may be associated with more than one image).

The above links via tags can be used, as the user reading the digital text printed on screen passes on the tag position with a highlighting or pointing tool, to send a command to the system to print on the screen or on the part of the screen 210 the corresponding image or images.

Furthermore, the other possibility of operation is rendered possible according to which the selection of the image by printing it on the screen allows to print on the screen the corresponding report and the corresponding completion part of the text.

When drafting the report, the completion part of the text chosen for insertion in the draft by the user according to one or more of the preceding embodiments also allows to insert as a short remark in a specifically provided field for comments associated with the image.

An image recognition processor may also be used to analyze each image and automatically select from a database of pre-drafted reports the appropriate report or at least suggest to the user a list of appropriate pre-drafted reports. With the term pre-drafted reports there are indicated already drafted reports associated with diagnostic images which are stored in a report and image database of a PACS or similar server units and which forms a collection of possible models or templates of reports.

Figure 6:
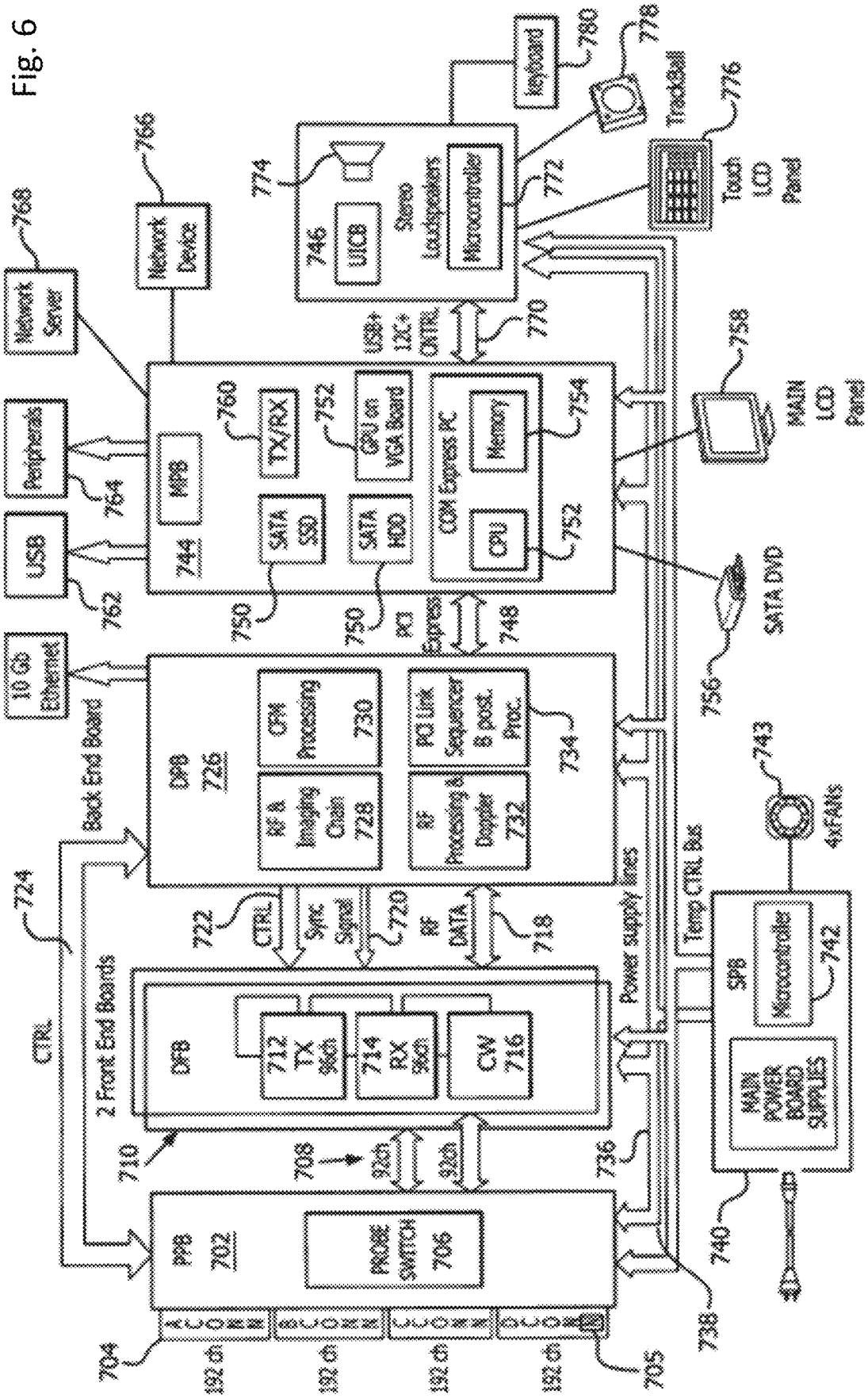
FIGS. 6 to 8 show the block diagrams of a further embodiment of an ultrasound system.

FIG. 6 illustrates a block diagram of an ultrasound system formed in accordance with an alternative embodiment. The system of FIG. 6 implements the operations described herein in connection with various embodiments. By way of example, one or more circuits/processors within the system implement the operations of any processes illustrated in connection with the figures and/or described herein. The system includes a probe interconnect board 702 that includes one or more probe connection ports 704. The connection ports 704 may support various numbers of signal channels (e.g., 128, 192, 256, etc.). The connector ports 704 may be configured to be used with different types of probe arrays (e.g., phased array, linear array, curved array, 1D, 1.25D, 1.5D, 1.75D, 2D array, etc.). The probes may be configured for different types of applications, such as abdominal, cardiac, maternity, gynecological, urological and cerebrovascular examination, breast examination and the like.

One or more of the connection ports 704 may support acquisition of 2D image data and/or one or more of the connection ports 704 may support 3D image data. By way of example only, the 3D image data may be acquired through physical movement (e.g., mechanically sweeping or physician movement) of the probe and/or by a probe that electrically or mechanically steers the transducer array.

The probe interconnect board (PIB) 702 includes a switching circuit 706 to select between the connection ports 704. The switching circuit 706 may be manually managed based on user inputs. For example, a user may designate a connection port 704 by selecting a button, switch or other input on the system. Optionally, the user may select a connection port 704 by entering a selection through a user interface on the system.

Optionally, the switching circuit 706 may automatically switch to one of the connection ports 704 in response to detecting a presence of a mating connection of a probe. For example, the switching circuit 706 may receive a "connect" signal indicating that a probe has been connected to a selected one of the connection ports 704. The connect signal may be generated by the probe when power is initially supplied to the probe when coupled to the connection port 704. Additionally, or alternatively, each connection port 704 may include a sensor 705 that detects when a mating connection on a cable of a probe has been interconnected with the corresponding connection port 704. The sensor 705 provides signal to the switching circuit 706, and in response thereto, the switching circuit 706 couples the corresponding connection port 704 to PIB outputs 708. Optionally, the sensor 705 may be constructed as a circuit with contacts provided at the connection ports 704. The circuit remains open when no mating connected is joined to the corresponding connection port 704. The circuit is closed when the mating connector of a probe is joined to the connection port 704.

A control line 724 conveys control signals between the probe interconnection board 702 and a digital processing board 726. A power supply line 736 provides power from a power supply 740 to the various components of the system, including but not limited to, the probe interconnection board (PIB) 702, digital front end boards (DFB) 710, digital processing board (DPB) 726, the master processing board (MPB) 744, and a user interface control board (UICB) 746. A temporary control bus 738 interconnects, and provides temporary control signals between, the power supply 740 and the boards 702, 710, 726, 744 and 746. The power supply 740 includes a cable to be coupled to an external AC power supply. Optionally, the power supply 740 may include one or more power storage devices (e.g. batteries) that provide power when the AC power supply is interrupted or disconnected. The power supply 740 includes a controller 742 that manages operation of the power supply 740 including operation of the storage devices.

Additionally, or alternatively, the power supply 740 may include alternative power sources, such as solar panels and the like. One or more fans 743 are coupled to the power supply 740 and are managed by the controller 742 to be turned on and off based on operating parameters (e.g. temperature) of the various circuit boards and electronic components within the overall system (e.g. to prevent overheating of the various electronics).

The digital front-end boards 710 providing analog interface to and from probes connected to the probe interconnection board 702. The DFB 710 also provides pulse or control and drive signals, manages analog gains, includes analog to digital converters in connection with each receive channel, provides transmit beamforming management and receive beamforming management and vector composition (associated with focusing during receive operations).

The digital front end boards 710 include transmit driver circuits 712 that generate transmit signals that are passed over corresponding channels to the corresponding transducers in connection with ultrasound transmit firing operations. The transmit driver circuits 712 provide pulse or control for each drive signal and transmit beamforming management to steer firing operations to points of interest within the region of interest. By way of example, a separate transmit driver circuits 712 may be provided in connection with each individual channel, or a common transmit driver circuits 712 may be utilized to drive multiple channels. The transmit driver circuits 712 cooperate to focus transmit beams to one or more select points within the region of interest. The transmit driver circuits 712 may implement single line transmit, encoded firing sequences, multiline transmitter operations, generation of shear wave inducing ultrasound beams as well as other forms of ultrasound transmission techniques.

The digital front end boards 710 include receive beamformer circuits 714 that received echo/receive signals and perform various analog and digital processing thereon, as well as phase shifting, time delaying and other operations in connection with beamforming. The beam former circuits 714 may implement various types of beamforming, such as single-line acquisition, multiline acquisition as well as other ultrasound beamforming techniques.

The digital front end boards 710 include continuous wave Doppler processing circuits 716 configured to perform continuous wave Doppler processing upon received echo signals. Optionally, the continuous wave Doppler circuits 716 may also generate continuous wave Doppler transmit signals.

The digital front-end boards 710 are coupled to the digital processing board 726 through various buses and control lines, such as control lines 722, synchronization lines 720 and one or more data bus 718. The control lines 722 and synchronization lines 720 provide control information and data, as well as synchronization signals, to the transmit drive circuits 712, receive beamforming circuits 714 and continuous wave Doppler circuits 716. The data bus 718 conveys RF ultrasound data from the digital front-end boards 710 to the digital processing board 726. Optionally, the digital front end boards 710 may convert the RF ultrasound data to I, Q data pairs which are then passed to the digital processing board 726.

The digital processing board 726 includes an RF and imaging module 728, a color flow processing module 730, an RF processing and Doppler module 732 and a PCI link module 734. The digital processing board 726 performs RF filtering and processing, processing of black and white image information, processing in connection with color flow, Doppler mode processing (e.g. in connection with polls wise and continuous wave Doppler). The digital processing board 726 also provides image filtering (e.g. speckle reduction) and scanner timing control. The digital processing board 726 may include other modules based upon the ultrasound image processing functionality afforded by the system.

The modules 728-734 comprise one or more processors, DSPs, and/or FPGAs, and memory storing program instructions to direct the processors, DSPs, and/or FPGAs to perform various ultrasound image processing operations. The RF and imaging module 728 performs various ultrasound related imaging, such as B mode related image processing of the RF data. The RF processing and Doppler module 732 convert incoming RF data to I, Q data pairs, and performs Doppler related processing on the I, Q data pairs. Optionally, the imaging module 728 may perform B mode related image processing upon I, Q data pairs. The CFM processing module 730 performs color flow related image processing upon the ultrasound RF data and/or the I, Q data pairs. The PCI link 734 manages transfer of ultrasound data, control data and other information, over a PCI express bus 748, between the digital processing board 726 and the master processing board 744.

The master processing board 744 includes memory 750 (e.g. serial ATA solid-state devices, serial ATA hard disk drives, etc.), a VGA board 752 that includes one or more graphic processing unit (GPUs), one or more transceivers 760 one or more CPUs 752 and memory 754. The master processing board (also referred to as a PC board) provides user interface management, scan conversion and cine loop management. The master processing board 744 may be connected to one or more external devices, such as a DVD player 756, and one or more displays 758. The master processing board includes communications interfaces, such as one or more USB ports 762 and one or more ports 764 configured to be coupled to peripheral devices. The master processing board 744 is configured to maintain communication with various types of network devices 766 and various network servers 768, such as over wireless links through the transceiver 760 and/or through a network connection (e.g. via USB connector 762 and/or peripheral connector 764).

The network devices 766 may represent portable or desktop devices, such as smart phones, personal digital assistants, tablet devices, laptop computers, desktop computers, smart watches, ECG monitors, patient monitors, and the like. The master processing board 744 conveys ultrasound images, ultrasound data, patient data and other information and content to the network devices for presentation to the user. The master processing board 744 receives, from the network devices 766, inputs, requests, data entry and the like.

The network server 768 may represent part of a medical network, such as a hospital, a healthcare network, a third-party healthcare service provider, a medical equipment maintenance service, a medical equipment manufacturer, a government healthcare service and the like. The communications link to the network server 768 may be over the Internet, a private intranet, a local area network, a wide-area network, and the like.

The master processing board 744 is connected, via a communications link 770 with a user interface control board 746. The communications link 770 conveys data and information between the user interface and the master processing board 744. The user interface control board 746 includes one or more processors 772, one or more audio/video components 774 (e.g. speakers, a display, etc.). The user interface control board 746 is coupled to one or more user interface input/output devices, such as an LCD touch panel 776, a trackball 778, a keyboard 780 and the like. The processor 772 manages operation of the LCD touch panel 776, as well as collecting user inputs via the touch panel 776, trackball 778 and keyboard 780, where such user inputs are conveyed to the master processing board 744 in connection with implementing embodiments herein.

Figure 7:
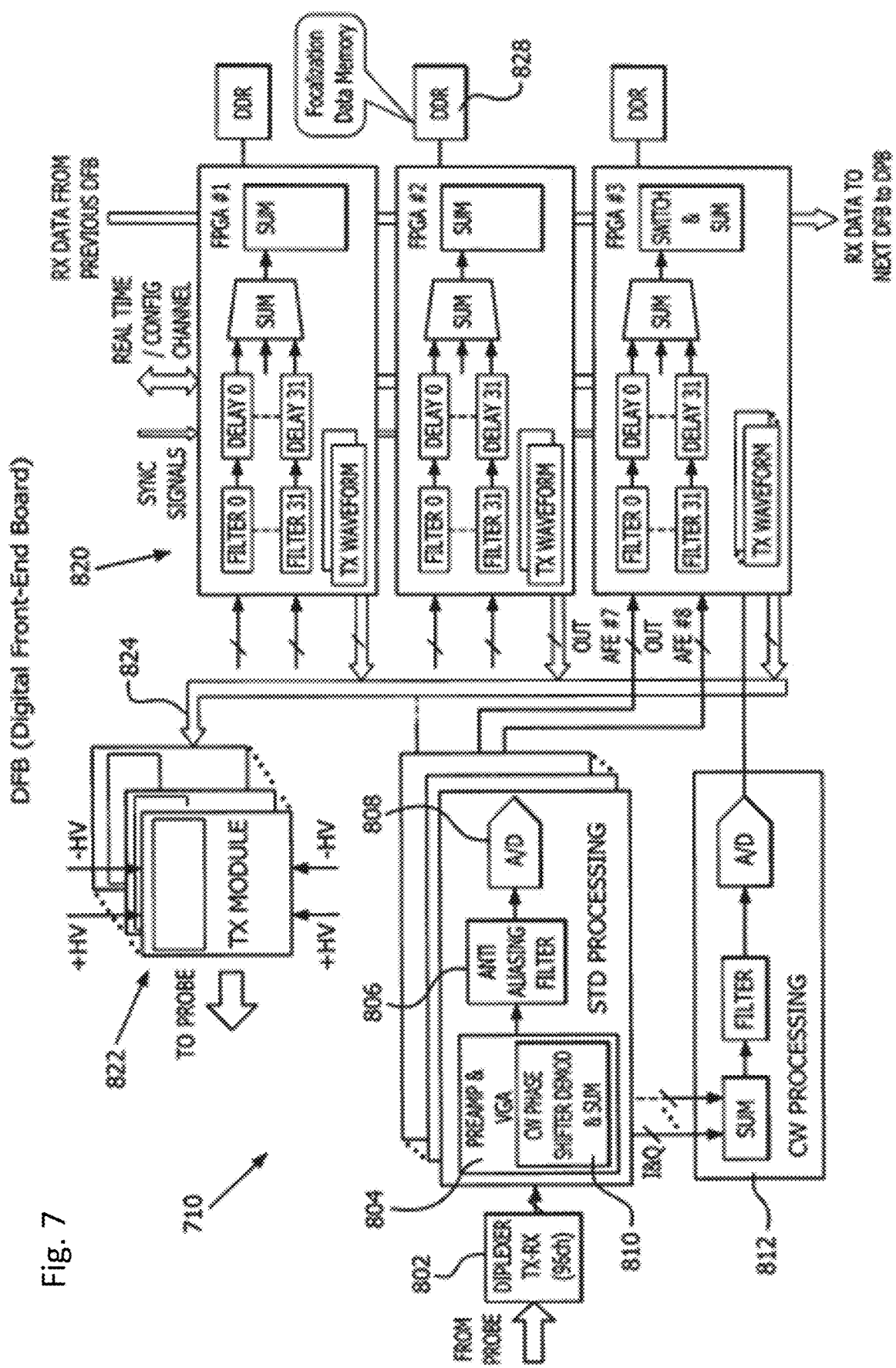

FIG. 7 illustrates a block diagram of a portion of the digital front-end boards 710 formed in accordance with embodiments herein. A group of diplexers 802 receive the ultrasound signals for the individual channels over the PIB output 708. The ultrasound signals are passed along a standard processing circuit 805 or to a continuous wave processing circuit 812, based upon the type of probing utilized. When processed by the standard processing circuit 805, a preamplifier and variable gain amplifier 804 process the incoming ultrasound receive signals that are then provided to an anti-aliasing filter 806 which performs anti-aliasing filtering.

According to an embodiment, the retrospective transmit beam focusing may be applied to the RF data directly acquired by the system or to transformed data according to different transformations as for example as a phase/quadrature (I/Q) transformation, or similar.

In the embodiment of FIG. 7 an example of the said transformation of the RF data is disclosed According to this example, the output of the filter 806 is provided to an A/D converter 808 that digitizes the incoming analog ultrasound receive signals. When a continuous wave (CW) probe is utilized, the signals therefrom are provided to a continuous wave phase shifter, demodulator and summer 810 which converts the analog RF receive signals to I,Q data pairs. The CW I,Q data pairs are summed, filtered and digitized by a continuous wave processing circuit 812. Outputs from the standard or continuous wave processing circuits 805, 812 are then passed to beam forming circuits 820 which utilize one or more FPGAs to perform filtering, delaying and summing the incoming digitized receive signals before passing the RF data to the digital processing board 726 (FIG. 6). The FPGAs receive focalization data from memories 828. The focalization data is utilized to manage the filters, delays and summing operations performed by the FPGAs in connection with beamforming. The beamformed RF or I/Q data is passed between the beamforming circuits 820 and ultimately to the digital processing board 726.

The digital front-end boards 710 also include transmit modules 822 that provide transmit drive signals to corresponding transducers of the ultrasound probe. The beamforming circuits 820 include memory that stores transmit waveforms. The transmit modules 822 receive transmit waveforms over line 824 from the beamforming circuits 820.

Figure 8:
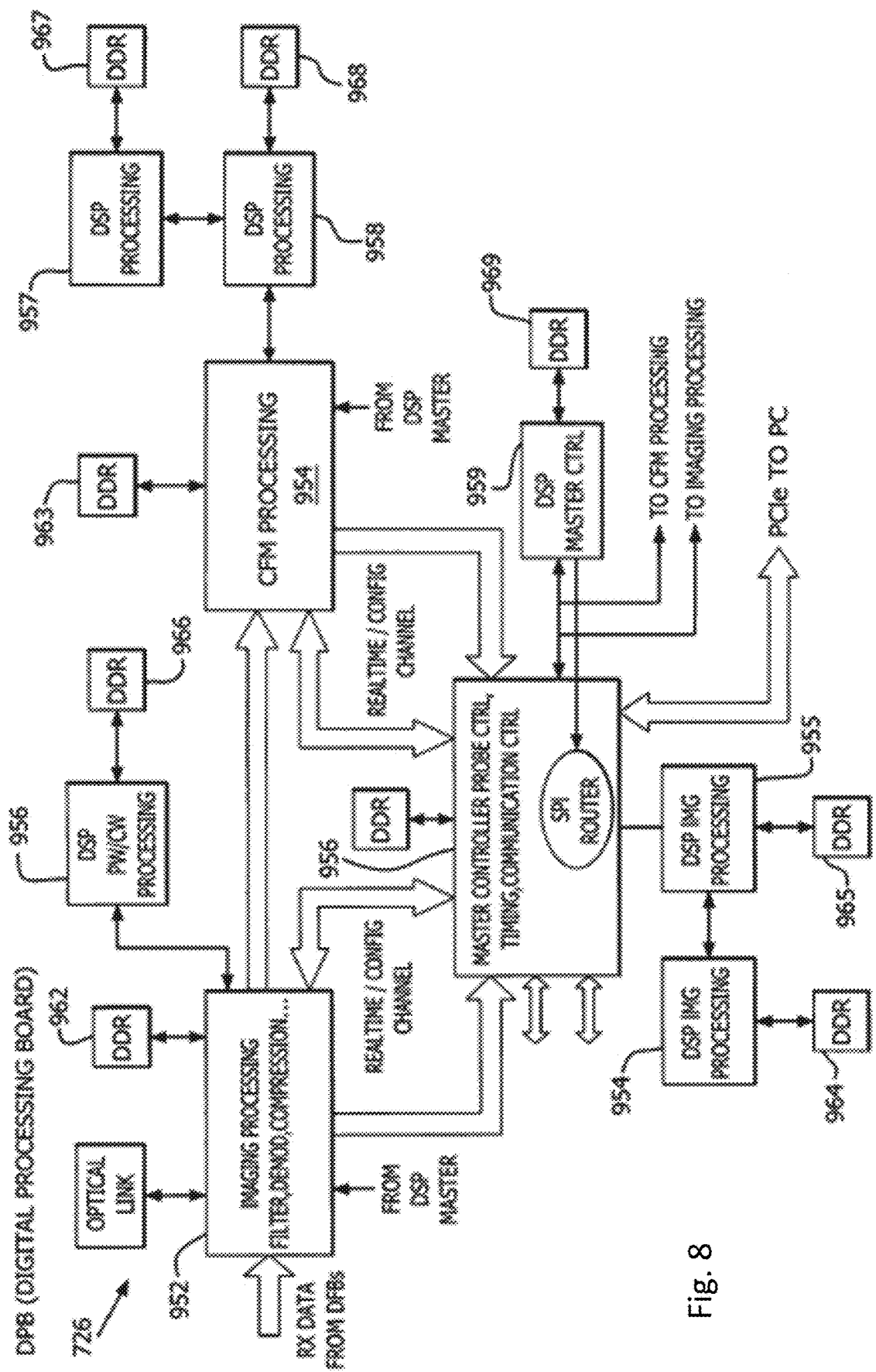

FIG. 8 illustrates a block diagram of the digital processing board 726 implemented in accordance with embodiments herein. The digital processing board 726 includes various processors 952-959 to perform different operations under the control of program instructions saved within corresponding memories see 962-969. A master controller 950 manages operation of the digital processing board 726 and the processors 952-959. By way of example, one or more processors as the 952 may perform filtering, the modulation, compression and other operations, while another processor 953 performs color flow processing. The master controller provides probe control signals, timing control signals, communications control and the like. The master controller 950 provides real-time configuration information and synchronization signals in connection with each channel to the digital front-end board 710.

Figure 9:
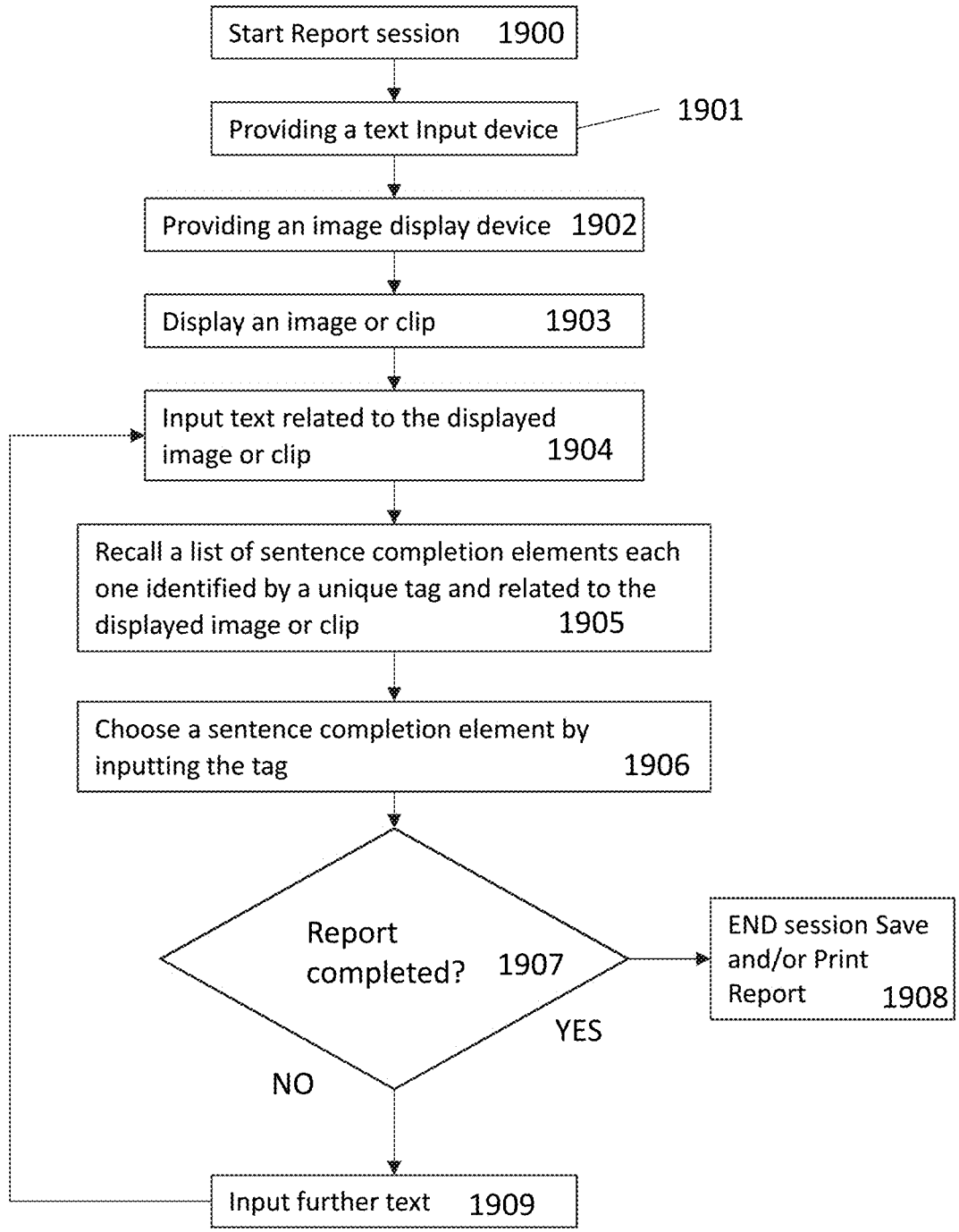
FIGS. 9 to 12 show four different embodiments of the workflow for carrying out the method according to embodiments herein.

FIG. 9 shows a first embodiment of a workflow for carrying out the method according to embodiments herein. The report session starts at step 1900. This report session may be carried out during imaging starting at any time after imaging start or after imaging has been carried out and completed. Text of the report is inserted or generated by a text input device 1901 which can be one chosen from the following list or a combination thereof: keyboard, speech recognition system, image recognition system.

The reported text is to be printed on a monitor as indicated at step 1902 and at step 1903 an image or clip generated by the ultrasound scanner is shown on the monitor. At step 1904 the report drafting process is started by inputting the text related to the display image. The text is inputted by one or more of the above indicated devices or systems and comprises a collateral part, which is not determined by the diagnostic content extracted from the images and a text completion part which contains the diagnostic information extracted from the images.

During drafting of the text of the report at predetermined insertion points in the said collateral part of the text a completion or a combination of completion parts of the text has to be inserted. This is carried out by recalling a list of sentence completion elements each one identified by a unique tag and related to the displayed image or clip at step 1905 and by the following step 1906 related to the choice of a sentence completion element by inputting the tag. If the report is not complete as determined at step 1907 than step 1909 of repeating steps 1904, 1905 and 1906 is carried out. If the report is complete the step 1908 is carried out consisting of ending the report draft session and saving and/or printing the completed report.

Figure 10:
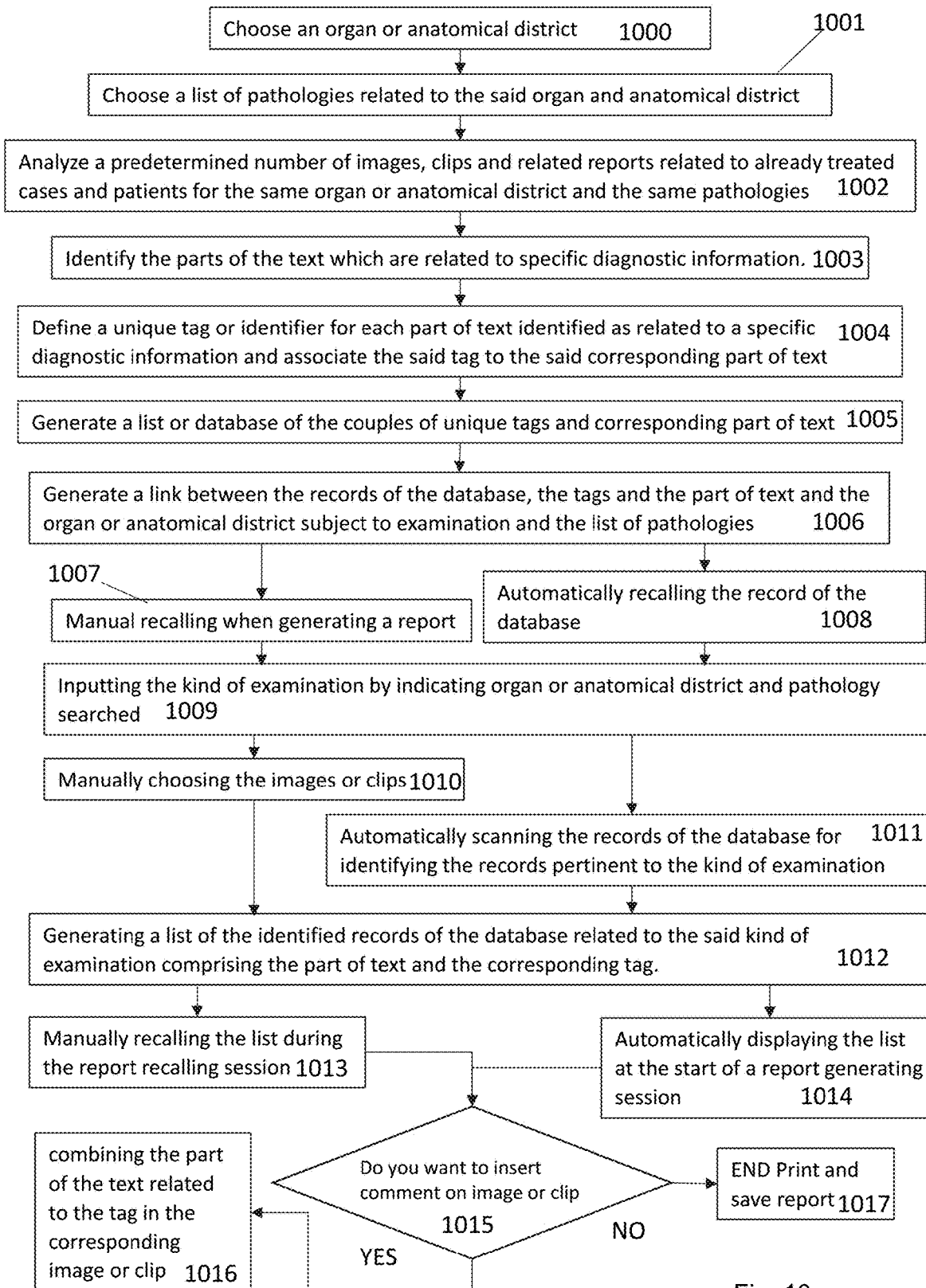

FIG. 10 shows a flow diagram of a workflow embodiment. According to this embodiment, at starting of the imaging session or at a certain instant during the imaging session or even at the end of the imaging session, the user selects at step 1000 an organ or an anatomic district. Further specification steps can be carried out as suggested by the exemplary step 1001 in which the user can choose a list of pathologies related to the said organ and anatomical district.

At step 1002 a predetermined number of cases is analyzed in relation to the images, clips and reports related to already treated cases and patients for the same organ or anatomical district and/or the same pathologies. A further variant could provide the step also of specifying the cases only related to the current user so to provide a closer correspondence of the report text to the expression style of the said user and provide higher degree of precision of the system.

Within the said collection of known cases analyzed at step 1002, at step 1003 and 1004 the parts of the text of the reports are identified which pertain to a specific diagnostic information and the said part of the texts of the existing already complete reports are associated with a unique tag. At step 1005 the identified parts of texts and the tags are saved in a database which records are represented by the pairs of unique tags and corresponding part of texts. Step 1006 provides for generating a link between the records of the database, the tags and the part of text and the organ or anatomical district subject to examination and the list of pathologies. At step 1006 the database for automatically identifying from the kind of imaging session the possible records is generated and the system is ready for operating the automatic or semiautomatic report draft.

Step 1007 and 1008 are related to two different kinds of use of the information provided by the database generated at step 1007. Both alternatives may be present in the system and may be chosen and activated by the user upon a selection and execute command. Step 1007 provides for a manual recalling of the tags and the associated list during drafting of the report each time the collateral text part needs to be complete by a specific completion part of the text including sensible information which in this case is the diagnostic information extracted from the images. Step 1008 provides for an automatic recalling of the tags and/or the associated list being controlled by the semantic of the collateral text, by indication determined from the samples.

By specifying the kind of examination by inputting the organ or the anatomical district and/or the pathology at step 1009, the list of pertinent tags and the corresponding list of completion text parts can be generated automatically or manually.

According to the embodiment providing for a manual operation images or clips representing the organ or anatomic district to be examined are chosen manually by the user at step 1010. The automatic alternative provided in step 1001 comprises automatically scanning the records of the database for identifying the records pertinent to the kind of examination.

In step 1012 there is provided a step of generating a list of the identified records of the database related to the said kind of examination comprising the part of text and the corresponding tag. Step 1013 provides for the manual recalling alternative embodiment, while step 1014 provides for the automatically displaying the list at the start of a report generating session.

The identified text completion part can be added to the image as a comment at step 1015 and this is suggested as an option to the user. When the answer is yes the step 1016 is carried out with the combining the part of the text related to the tag in the corresponding image or clip. When the answer is no, then step 1017 is carried out with the terminating the workflow and printing and/or saving the complete report. The approved completed report together with the images and the diagnostic information can be used also to upgrade the database and the algorithm processing the data in order to provide a higher precision for the future processes.

Figure 11:
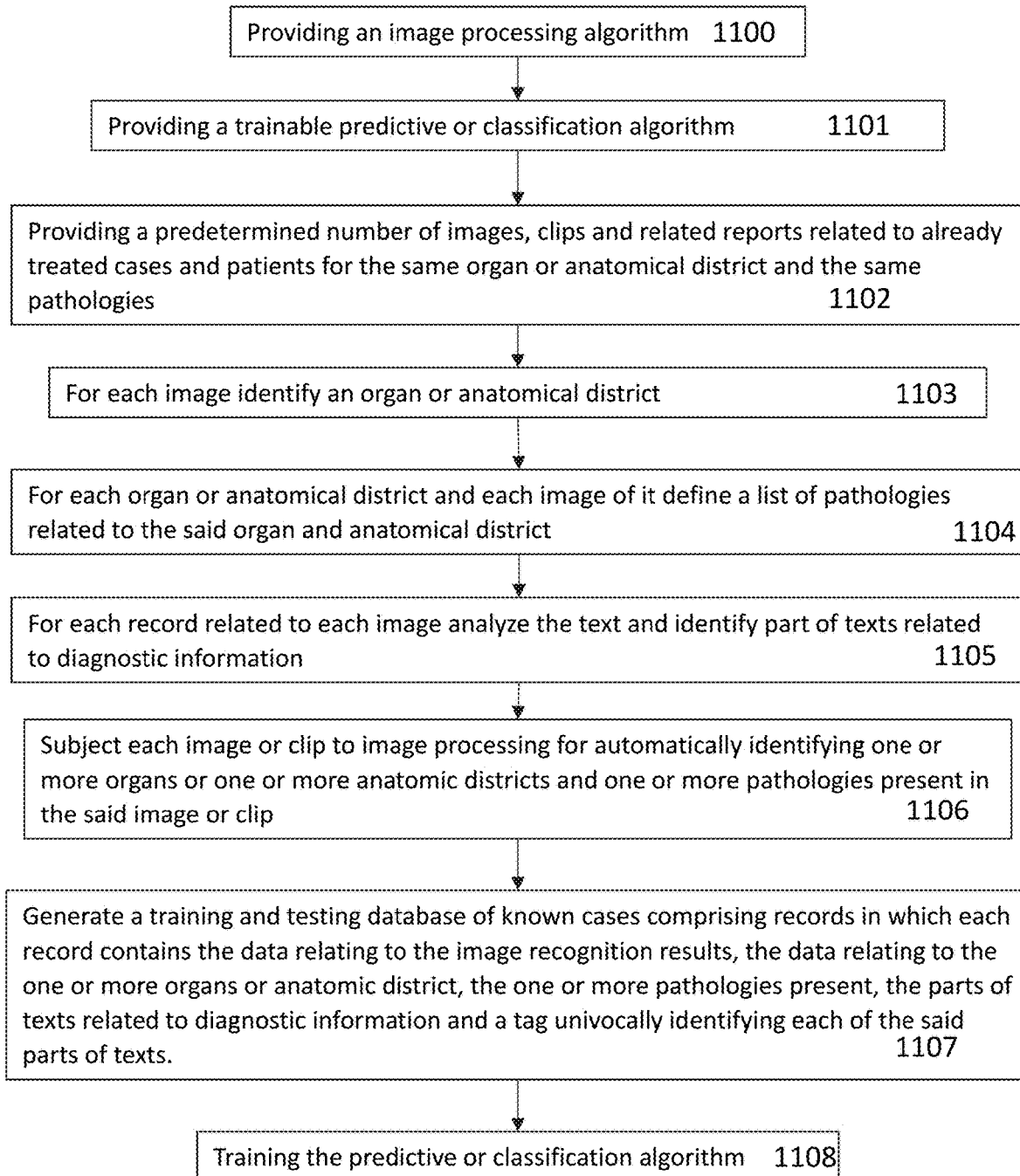

The workflow of FIG. 11 describes an embodiment with providing an automatic generation of the database of reports the contained collateral parts and completion parts of text and the associated kind of organ and/or anatomic district and/or images and/or pathologies and/or kind of imaging session. At step 1100 an image processing algorithm is provided and at step 1101 a trainable predictive or classification algorithm is provided. At step 1102 a predetermined number of images, clips and related reports related to already treated cases and patients for the same organ or anatomical district and the same pathologies are provided. As indicated by step 1103 for each image an organ or an anatomic district is identified and at step 1104 for each organ or anatomical district and for each image of it a list of possible pathologies is generated.

At step 1105, for each record related to each image the text of the reports is analyzed and the part of texts related to diagnostic information extracted from the said images is determined. At step 1006 each image is subjected to image processing for automatically identifying one or more organs or one or more anatomic districts and one or more pathologies present in the said image or clip. This data is used to generate a training and testing database of known cases comprising records in which each record contains the data relating to the image recognition results, the data relating to the one or more organs or anatomic district, the one or more pathologies present, the parts of texts related to diagnostic information and a tag univocally identifying each of the said parts of texts. This database is then used to train the predictive or the classification algorithm to be used for executing the process according to one of the described embodiments and particularly the automatic variant of the embodiment of FIG. 10.

Figure 12:
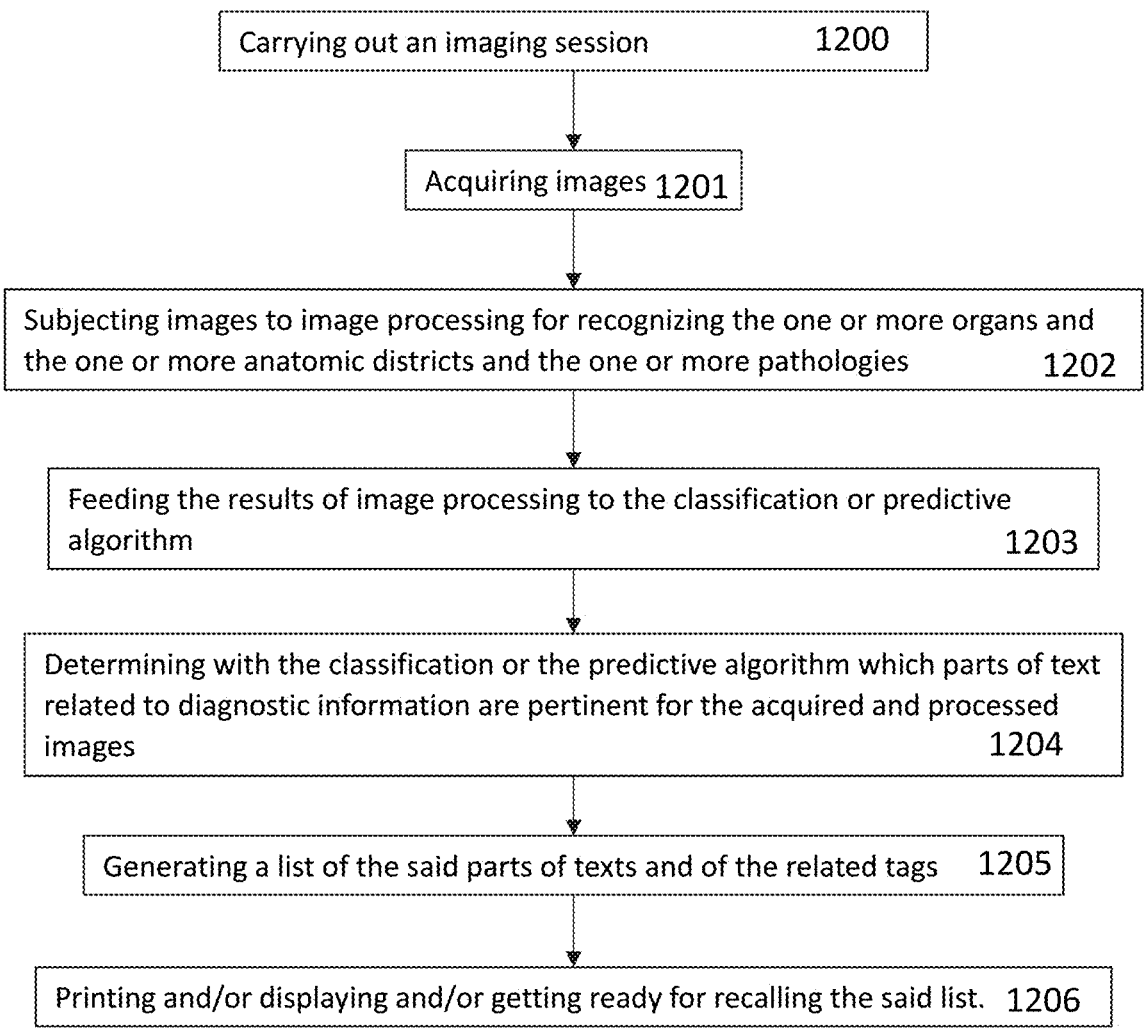

FIG. 12 shows the workflow comprising the steps for using the said classification or predictive algorithm generated according to the previous example of FIG. 11. At step 1200 an imaging session is started and during execution images are acquired as indicated by 1201.

At step 1202, images are subjected to image processing for recognizing the one or more organs and the one or more anatomic districts and the one or more pathologies. At step 1203 the results of image processing are fed to the classification or predictive algorithm. According to step 1204, the classification or the predictive algorithm is used to determine which parts of text related to diagnostic information are pertinent for the acquired and processed images. Step 1205 provides for generating a list of the said parts of texts and of the related tags and at step 1206 the said list can be printed and/or displayed and/or set ready for being recalled by the user drafting the report.

It should be clearly understood that the various arrangements and processes broadly described and illustrated with respect to the figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

Aspects are described herein with reference to the figures, which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

One or more of the operations described above in connection with the methods may be performed using one or more processors. The different devices in the systems described herein may represent one or more processors, and two or more of these devices may include at least one of the same processors. In one embodiment, the operations described herein may represent actions performed when one or more processors (e.g., of the devices described herein) execute program instructions stored in memory (for example, software stored on a tangible and non-transitory computer readable storage medium, such as a computer hard drive, ROM, RAM, or the like).

The processor(s) may execute a set of instructions that are stored in one or more storage elements, in order to process data. The storage elements may also store data or other information as desired or needed. The storage element may be in the form of an information source or a physical memory element within the controllers and the controller device. The set of instructions may include various commands that instruct the controllers and the controller device to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

The controller may include any processor-based or microprocessor-based system including systems using microcontrollers, reduced instruction set computers (RISC), application specific integrated circuitry (ASICs), field-programmable gate arrays (FPGAs), logic circuitry, and any other circuit or processor capable of executing the functions described herein. When processor-based, the controller executes program instructions stored in memory to perform the corresponding operations. Additionally or alternatively, the controllers and the controller device may represent circuitry that may be implemented as hardware. The above examples are exemplary only and are thus not intended to limit in any way the definition and/or meaning of the term "controller."

Optionally, aspects of the processes described herein may be performed over one or more networks one a network server. The network may support communications using any of a variety of commercially-available protocols, such as Transmission Control Protocol/Internet Protocol ("TCP/IP"), User Datagram Protocol ("UDP"), protocols operating in various layers of the Open System Interconnection ("OSI") model, File Transfer Protocol ("FTP"), Universal Plug and Play ("UpnP"), Network File System ("NFS"), Common Internet File System ("CIFS") and AppleTalk. The network can be, for example, a local area network, a wide-area network, a virtual private network, the Internet, an intranet, an extranet, a public switched telephone network, an infrared network, a wireless network, a satellite network and any combination thereof.

In embodiments utilizing a web server, the web server can run any of a variety of server or mid-tier applications, including Hypertext Transfer Protocol ("HTTP") servers, FTP servers, Common Gateway Interface ("CGI") servers, data servers, Java servers, Apache servers and business application servers. The server(s) also may be capable of executing programs or scripts in response to requests from user devices, such as by executing one or more web applications that may be implemented as one or more scripts or programs written in any programming language, such as Java®, C, C# or C++, or any scripting language, such as Ruby, PHP, Perl, Python or TCL, as well as combinations thereof. The server(s) may also include database servers, including without limitation those commercially available from Oracle®, Microsoft®, Sybase® and IBM® as well as open-source servers such as MySQL, Postgres, SQLite, MongoDB, and any other server capable of storing, retrieving and accessing structured or unstructured data. Database servers may include table-based servers, document-based servers, unstructured servers, relational servers, non-relational servers or combinations of these and/or other database servers.

The embodiments described herein may include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer or speaker). Such a system may also include one or more storage devices, such as disk drives, optical storage devices and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims and described in the present disclosure.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims and described in the present disclosure.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

Preferred embodiments of this disclosure are described herein. Variations of those preferred embodiments may become apparent to those of ordinary skill in the art upon reading the foregoing description. The inventors expect skilled artisans to employ such variations as appropriate and the inventors intend for embodiments of the present disclosure to be practiced otherwise than as specifically described herein. Accordingly, the scope of the present disclosure includes all modifications and equivalents of the subject matter recited in the claims appended hereto as permitted by applicable law. Moreover, any combination of the above-described elements in all possible variations thereof is encompassed by the scope of the present disclosure unless otherwise indicated herein or otherwise clearly contradicted by context.

All references, including publications, patent applications and patents, cited herein are hereby incorporated by reference to the same extent as if each reference were individually and specifically indicated to be incorporated by reference and were set forth in its entirety herein.

The invention claimed is:

1. A method for generating medical reports based on a medical image or a sequence of medical images acquired within an imaging examination session, which method comprises:
   visualizing the image or sequence of images;
   carrying out a report text generation step by using a speech recognition process while visualizing the image or the sequence of images;
   saving the report text by associating uniquely the report text to the visualized image or sequence of images,
   wherein tags are provided at selected positions in the report text, each tag being associated with a list of possible completion text parts relating to a description of results of the analysis of examination results from which a completion text part is selected and inserted into the report text at a position that corresponds to the tag,
   each element of said list being identified by a key having a unique identification that is vocally or non-vocally selectable by a user when that key is selected, the list being either automatically visualized to the user at a corresponding one of the selected positions in the report text or recalled by the user by a vocal command or a user interface input, the selected positions in the report text comprising predetermined positions in the report text, and any position in the report text at which the user selects a key, the completion text part of the text associated with the selected key being inserted in the report text at a position that corresponds to when the selected key is selected; and
   determining a position, quantity, unique identification of each completion text part key, and corresponding completion text part by selecting an anatomic district and/or an examination protocol and/or a specific pathology; providing a plurality of different existing reports based on the examination of the above selected anatomic district and/or an examination protocol and/or a specific pathology; providing an algorithm for carrying out a semantic analysis of a selected number of the existing reports to determine different parts of the text of the analyzed existing reports, those parts of the text of the existing reports which are similar from one existing report to another existing report among the analyzed existing reports being classified as collateral text parts, those parts of the text of the analyzed existing reports describing different results of a diagnosis based on the examination results being classified as completion text parts of the collateral text parts;
   associating the tags to the collateral parts at predetermined positions of the report text, the tags being related to respective ones of a list of the completion text parts of the text of the analyzed reports describing the different results of the diagnosis based on the examination of the above selected anatomic district and/or an examination protocol and/or a specific pathology;
   associating to each of the completion text parts a key having a unique identification, wherein the key is used as a command by the user when selecting and inserting the corresponding completion text part in a collateral text part at a position in the report text that is associated with the tag.

2. A method according to claim 1, wherein the visualizing comprises:
   carrying out an imaging examination to acquire an image or a sequence of images; and
   visualizing the image or the sequence of images acquired during the imaging examination.

3. A method according to claim 1,
   wherein the speech recognition process is performed to create the report text, or an integration file note related to the acquired images or sequence of images, while performing the image acquisition.

4. A method according to claim 1,
   wherein starting of the speech recognition process is caused by a command given by the user or by an image recognition process acquiring and analyzing images of a face of the user when speaking and determining when the user begins to speak,
   the image recognition process recognizing words or commands which are given by the user by inaudible speaking.

5. A method according to claim 1,
   wherein the report text generation step comprises an interactive reporting process which automatically populates statements into a corresponding text region of the report based on the speech recognition process.

6. A method according to claim 5,
   wherein the interactive reporting process comprises an interactive text completion step comprising a suggestion to the user of a series of possible sentence completion parts, wherein such sentence completion parts are uniquely associated with a sentence completion tag, said tag being an alphanumeric key the user vocally or non-vocally selects to add sentence completion part, at the corresponding position, to the text generated by the speech recognition process.

7. A method according to claim 1, wherein each report of the plurality of different existing reports is further associated with a physician or sonographer who has generated the existing report and the algorithm is taught to recognize automatically, or upon user input, the specific physician or sonographer and suggest a collateral text part or at least a selected number of the collateral text parts, the corresponding collateral text part tags, and a list of examination results which are generated by analyzing the reports of the physician or sonographer.

8. A method according to claim 1, wherein a link is generated between content of the image or the sequence of images and at least the completion text part describing the results on the corresponding image or sequence of images, the link being such that, when in a report the completion text part or the related completion text tag is selected, the corresponding image or sequence of images is automatically retrieved and visualized or, when a certain image is selected, the list of possible completion text parts is visualized.

9. A method according to claim 1, further comprising carrying out an image recognition step in which content of the image or the sequence of images is automatically identified and recognized, a link being provided between the image and a completion text part suggestion corresponding to the recognized content of the image or the sequence of images.

10. A method according to claim 8, wherein the link between the content of the image and at least the completion text part describing the results on the corresponding image or sequence of images is such that, when a certain image is selected, a corresponding list of alternatives of the completion text part is visualized to the user depending on the results of the examination and the user carries out a selection of the completion text part.

11. A system for generating medical reports comprising: a scanner unit for acquiring data from a target object of a patient; a processing unit for generating one or more images of the patient from the data acquired by the scanner unit; at least one monitor for visualizing one or more of the images and/or a time sequence of said images;
a user interface comprising input devices for selecting commands from a list of commands visualized on the at least one monitor and/or for inputting data or commands and output devices;
a word processor for generating text in digital format, the word processor comprising an input for inputting text and/or commands and an output for showing the inputted text and/or the available commands;
a memory in which a database of a plurality of existing reports is saved and from which one or more of completion text parts are retrieved and made ready to be inserted in a report by user selection and insertion commands,
wherein the database is configured such that each one of the plurality of existing reports is divided into a collateral text part and a completion text part, the collateral text part being content that is not directly related to the content of the image or images but instead describes one or more collateral features defining the target object of the examination, the kind of examination, the examination protocol, and the anatomic district of the patient, and the completion text part describing the content of each image according to different alternatives possible for the content,
wherein the content of the images and the collateral text parts correspond to the one or more collateral features defining the target object of the examination and/or the kind of examination and/or the examination protocol and/or the anatomic district, and
wherein the completion text parts are associated with respective unique selection keys, and the collateral text parts are provided in a user-generated report with tags that indicate a point of insertion of a selected one of the completion text parts into the user-generated report, the tags automatically suggesting one of the completion text parts by visualizing a list of different completion text parts or the unique selection keys signaling to the user that a list of completion text parts is available and are retrieved and visualized by a command comprising one of the unique selection keys; and
a database generation unit comprising a classifier processor configured to analyze different ones of the existing reports and the corresponding images on which the different ones of the existing reports have been based and for identifying collateral text parts and completion text parts therein, the classifier processor being configured to generate links between the images in the different ones of the existing reports and the corresponding collateral text parts and completion text parts identified by the classifier processor, the collateral text parts and completion text parts identified by the classifier processor being stored in the database, and respective unique selection keys corresponding to the completion text parts identified by the classifier processor being stored in the database;
wherein the memory or a different memory is configured for saving the user-generated report formed by the combination of the chosen collateral text parts and completion text parts.

12. A system according to claim 11, comprising as input for the word processor a speech recognition and/or text dictation unit comprising at least one microphone.

13. A system according to claim 11, the at least one monitor comprising at least two monitors, a first monitor for showing the images and related graphics and data, and a second monitor, which may be a touch-screen type, for showing, the part of the user-generated report appearing on the first monitor being hidden or substituted by a different graphics/contents.

14. A system according to claim 11, the at least one monitor comprising a main screen and a touch screen/interactive user interface of the system, and further comprising anti-visibility filters or special screen highly sensitive direction polarization both for the main screen and the touch screen/interactive user interface for maintaining full privacy protection of the patient.

* * * * *